(12) United States Patent
Deutschle et al.

(10) Patent No.: US 11,034,477 B2
(45) Date of Patent: Jun. 15, 2021

(54) METHOD OF TRANSFERRING A PLURALITY OF CONTAINERS AND/OR CLOSURE ELEMENTS INTO A CLEAN ROOM, TRANSPORT AND PACKAGING CONTAINER AND PACKAGING STRUCTURE THEREFORE

(71) Applicant: SCHOTT AG, Mainz (DE)

(72) Inventors: Gregor Fritz Deutschle, Idstein (DE); Edgar Pawlowski, Stadecken-Elsheim (DE)

(73) Assignee: SCHOTT AG, Mainz (DE)

( * ) Notice: Subject to any disclaimer, the term of this patent is extended or adjusted under 35 U.S.C. 154(b) by 777 days.

(21) Appl. No.: 15/442,941

(22) Filed: Feb. 27, 2017

(65) Prior Publication Data

US 2017/0247132 A1    Aug. 31, 2017

(30) Foreign Application Priority Data

Feb. 26, 2016    (DE) .......................... 102016103404.5

(51) Int. Cl.
| | |
|---|---|
| *B65B 55/02* | (2006.01) |
| *A61J 1/16* | (2006.01) |
| *B65B 43/46* | (2006.01) |
| *B65B 5/06* | (2006.01) |
| *B65B 55/04* | (2006.01) |
| *B65D 25/10* | (2006.01) |
| *B65D 77/20* | (2006.01) |

(Continued)

(52) U.S. Cl.
CPC .............. *B65B 55/027* (2013.01); *A61J 1/00* (2013.01); *A61J 1/16* (2013.01); *B01L 1/02* (2013.01); *B65B 5/06* (2013.01); *B65B 43/46* (2013.01); *B65B 55/04* (2013.01); *B65D 25/108* (2013.01); *B65D 77/2032* (2013.01); *A61B 50/30* (2016.02); *B01L 3/527* (2013.01); *B01L 9/06* (2013.01); *G21F 7/005* (2013.01)

(58) Field of Classification Search
None
See application file for complete search history.

(56) References Cited

U.S. PATENT DOCUMENTS

| | | |
|---|---|---|
| 832,086 A | 10/1906 | Schweitzer |
| 3,682,208 A | 8/1972 | Fedi |

(Continued)

FOREIGN PATENT DOCUMENTS

| | | |
|---|---|---|
| CN | 102665795 | 9/2012 |
| CN | 101945673 | 3/2014 |

(Continued)

*Primary Examiner* — Hemant Desai
*Assistant Examiner* — Tanzim Imam
(74) *Attorney, Agent, or Firm* — Ohlandt, Greeley, Ruggiero & Perle, L.L.P.

(57) ABSTRACT

A transport and packaging container for a plurality of pharmaceutical containers and a method for transferring the pharmaceutical containers from the transport and packaging containers into a clean room are provided. By placing a side wall of the transport and packaging container in close proximity to or in contact with the side wall of the clean room and by opening the side wall of the transport and packaging container and a transfer port door of the clean room, the pharmaceutical containers can be transferred into the inside space of the clean room via the access opening.

21 Claims, 34 Drawing Sheets

(51) Int. Cl.
*A61J 1/00* (2006.01)
*B01L 1/02* (2006.01)
B01L 9/06 (2006.01)
B01L 3/00 (2006.01)
A61B 50/30 (2016.01)
G21F 7/005 (2006.01)

(56) References Cited

U.S. PATENT DOCUMENTS

| | | | |
|---|---|---|---|
| 5,323,569 A | 6/1994 | Walz | |
| 5,372,787 A | 12/1994 | Ritter | |
| 5,421,626 A * | 6/1995 | Glachet | B01L 1/02 220/318 |
| 5,460,439 A * | 10/1995 | Jennrich | B01L 1/02 312/1 |
| 5,783,156 A * | 7/1998 | Renzi | F26B 5/06 312/1 |
| 6,705,061 B1 | 3/2004 | Porret | |
| 6,817,143 B2 * | 11/2004 | Porret | B01L 1/02 49/507 |
| 7,252,800 B2 | 8/2007 | Jacobs | |
| 7,766,164 B2 | 8/2010 | Hurst | |
| 8,118,167 B2 | 2/2012 | Togashi | |
| 2004/0228759 A1 | 11/2004 | Frost | |
| 2005/0042710 A1 | 2/2005 | Oshima | |
| 2009/0100802 A1 | 4/2009 | Bush | |
| 2011/0024419 A1 | 2/2011 | Gabel | |
| 2011/0132797 A1 | 6/2011 | Adair | |
| 2013/0006213 A1 | 1/2013 | Arnitz | |
| 2013/0161225 A1 | 6/2013 | Lepot | |
| 2014/0027332 A1 | 1/2014 | Pawlowski | |
| 2014/0230963 A1 | 8/2014 | Simon | |
| 2014/0291995 A1 | 10/2014 | Chavrot | |
| 2015/0053703 A1 | 2/2015 | Kreidler | |
| 2015/0114853 A1 | 4/2015 | Rossmann | |
| 2015/0114871 A1 | 4/2015 | Fitzpatrick | |
| 2015/0166217 A1 | 6/2015 | Deutschle | |

FOREIGN PATENT DOCUMENTS

| | | |
|---|---|---|
| DE | 1017454 | 10/1957 |
| DE | 69307433 | 7/1997 |
| DE | 69506008 | 4/1999 |
| DE | 69614592 | 5/2002 |
| DE | 10341978 | 9/2004 |
| DE | 202005011058 | 9/2005 |
| DE | 202007015886 | 1/2008 |
| DE | 202013007581 | 9/2013 |
| DE | 102013114404 | 6/2015 |
| EP | 2091051 | 8/2009 |
| EP | 2659981 | 11/2013 |
| EP | 2183166 | 10/2014 |
| FR | 2595667 | 9/1987 |
| GB | 2478703 | 9/2011 |
| WO | 9534078 | 12/1995 |
| WO | 0012388 | 3/2000 |
| WO | 2010086128 | 8/2010 |
| WO | 2015023924 | 2/2015 |

* cited by examiner

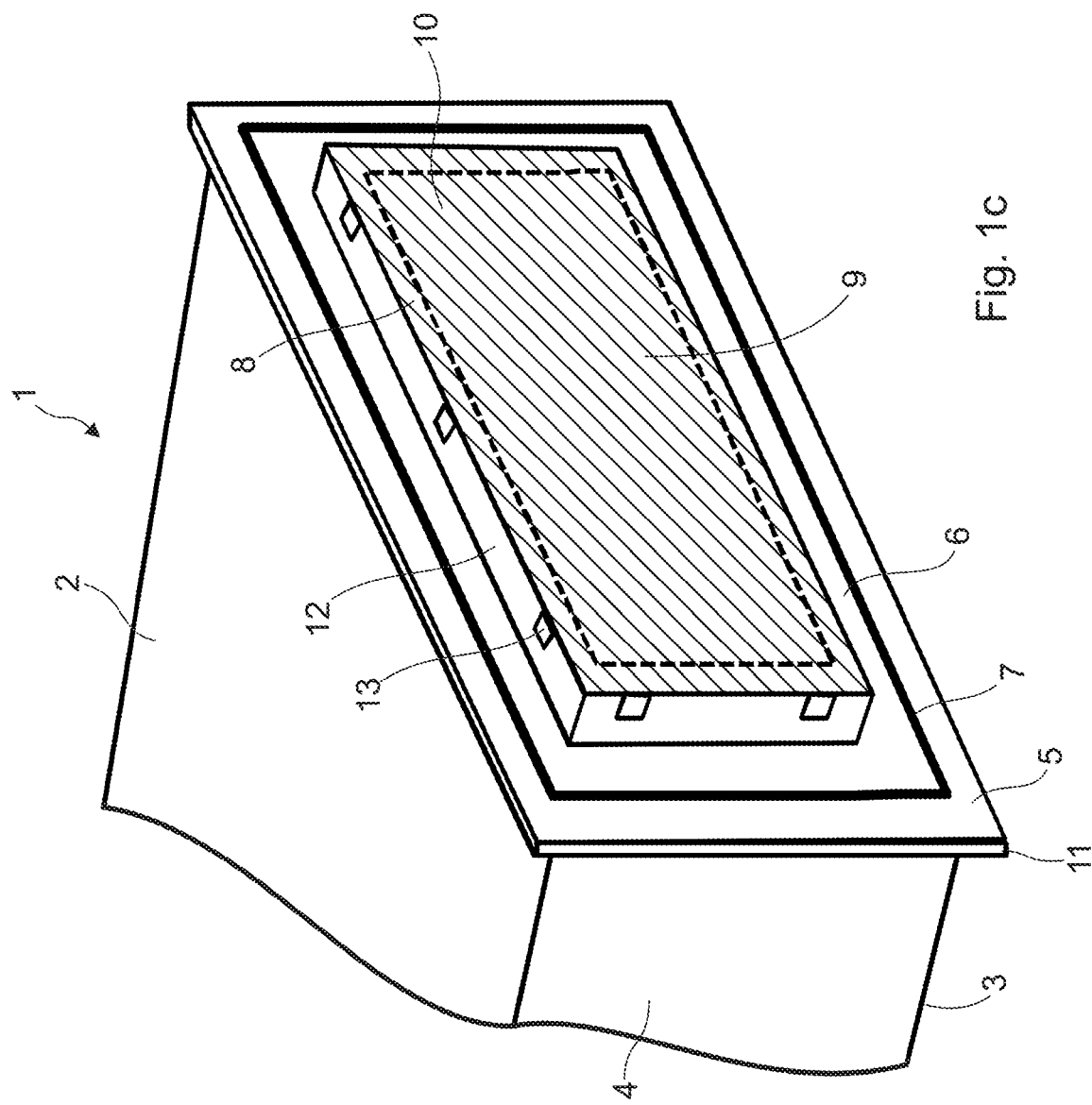

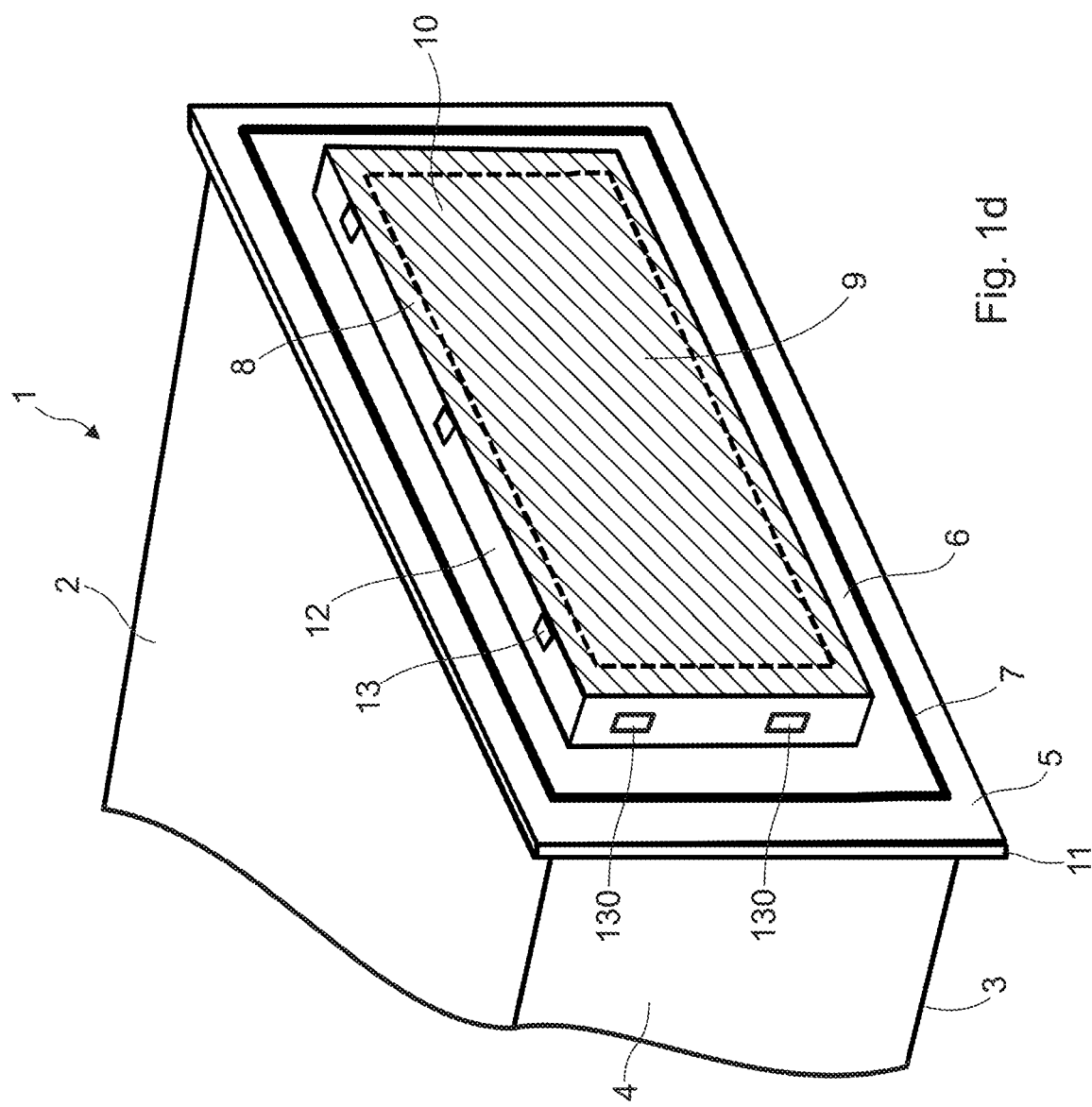

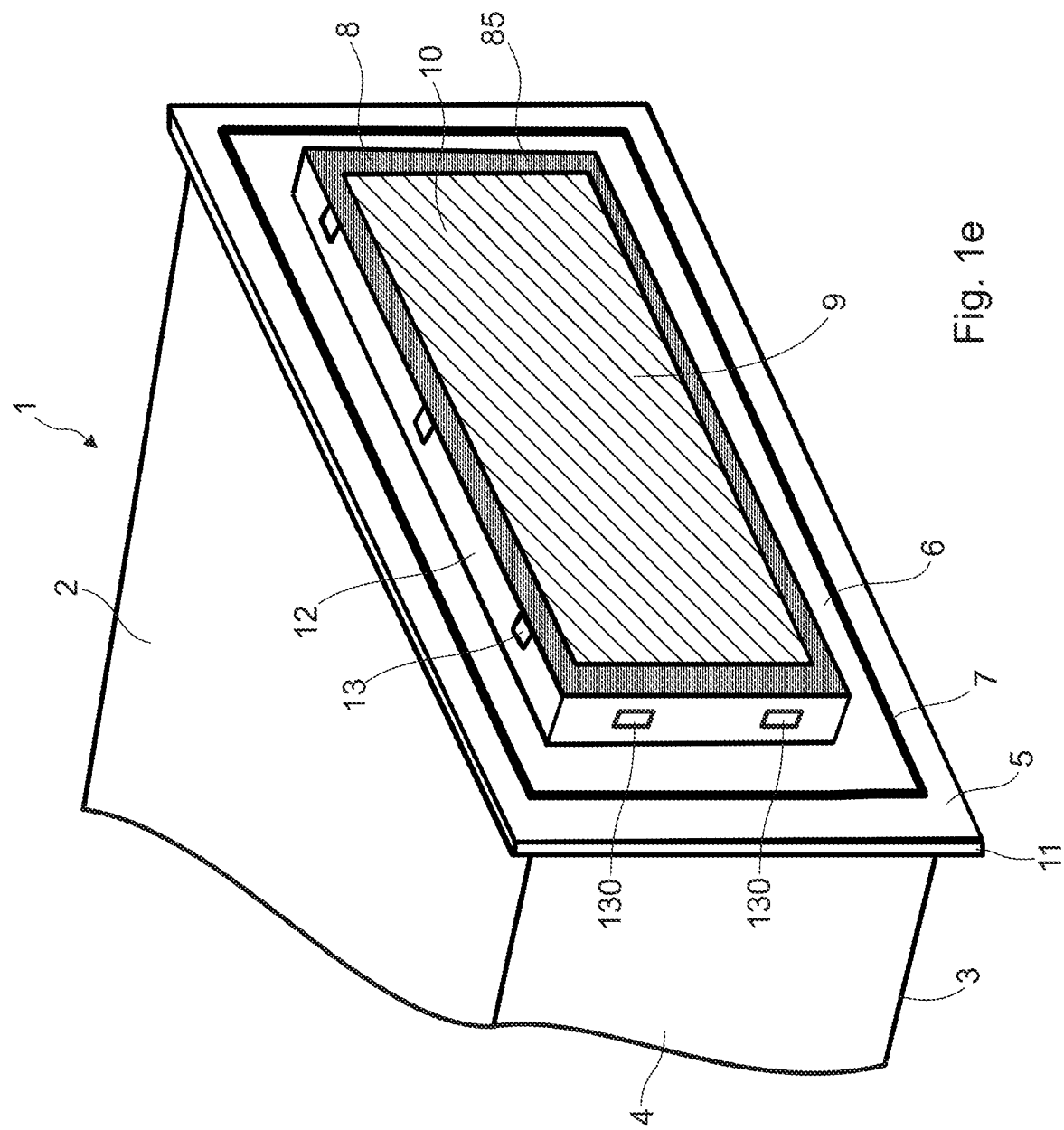

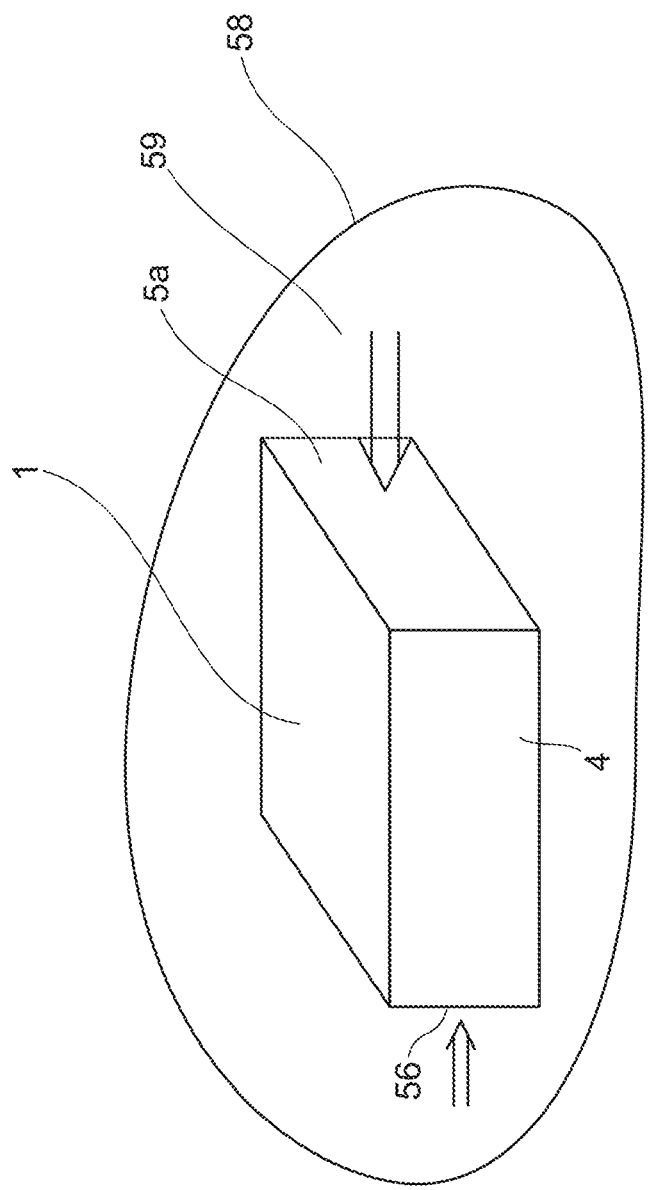

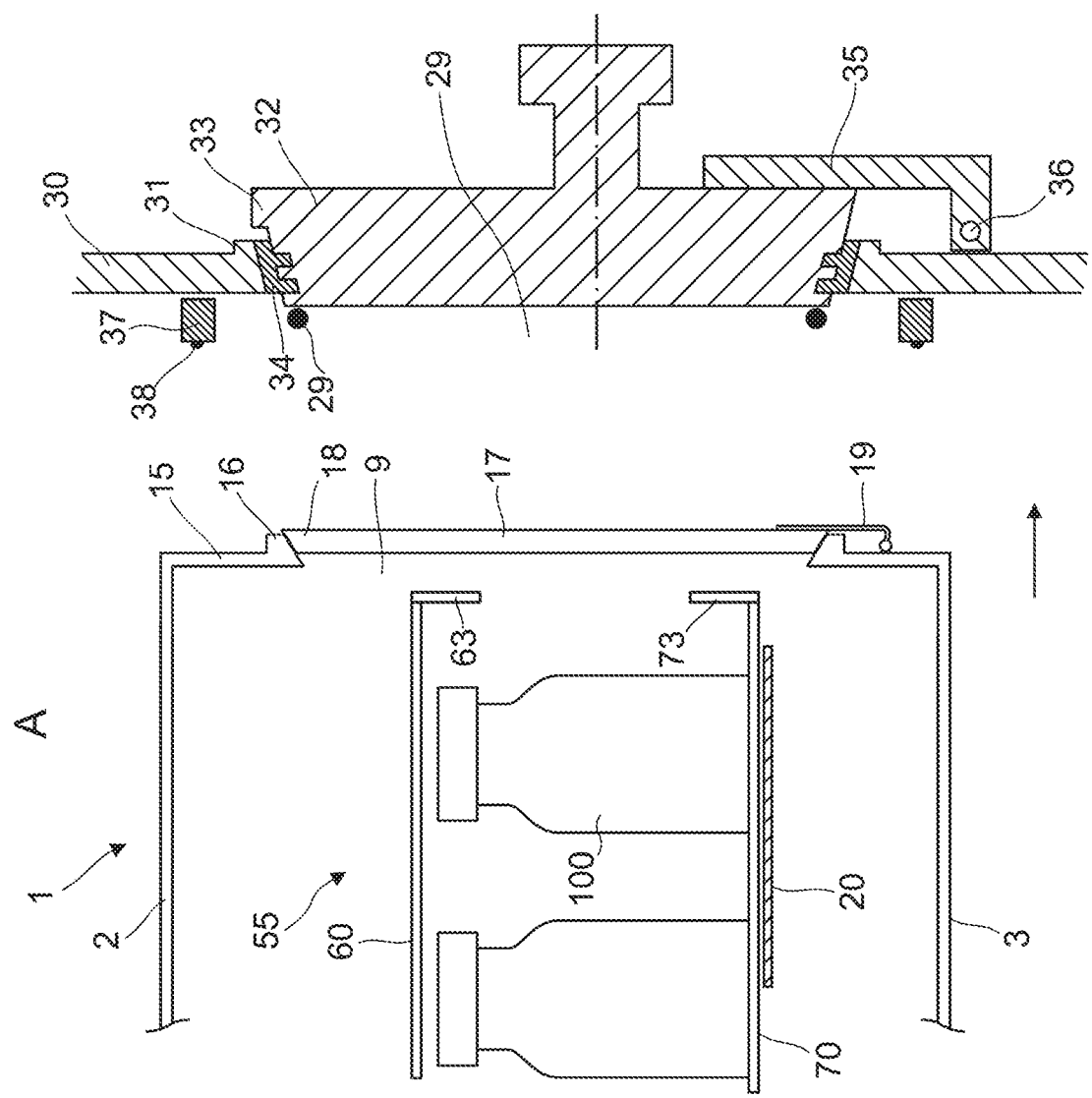

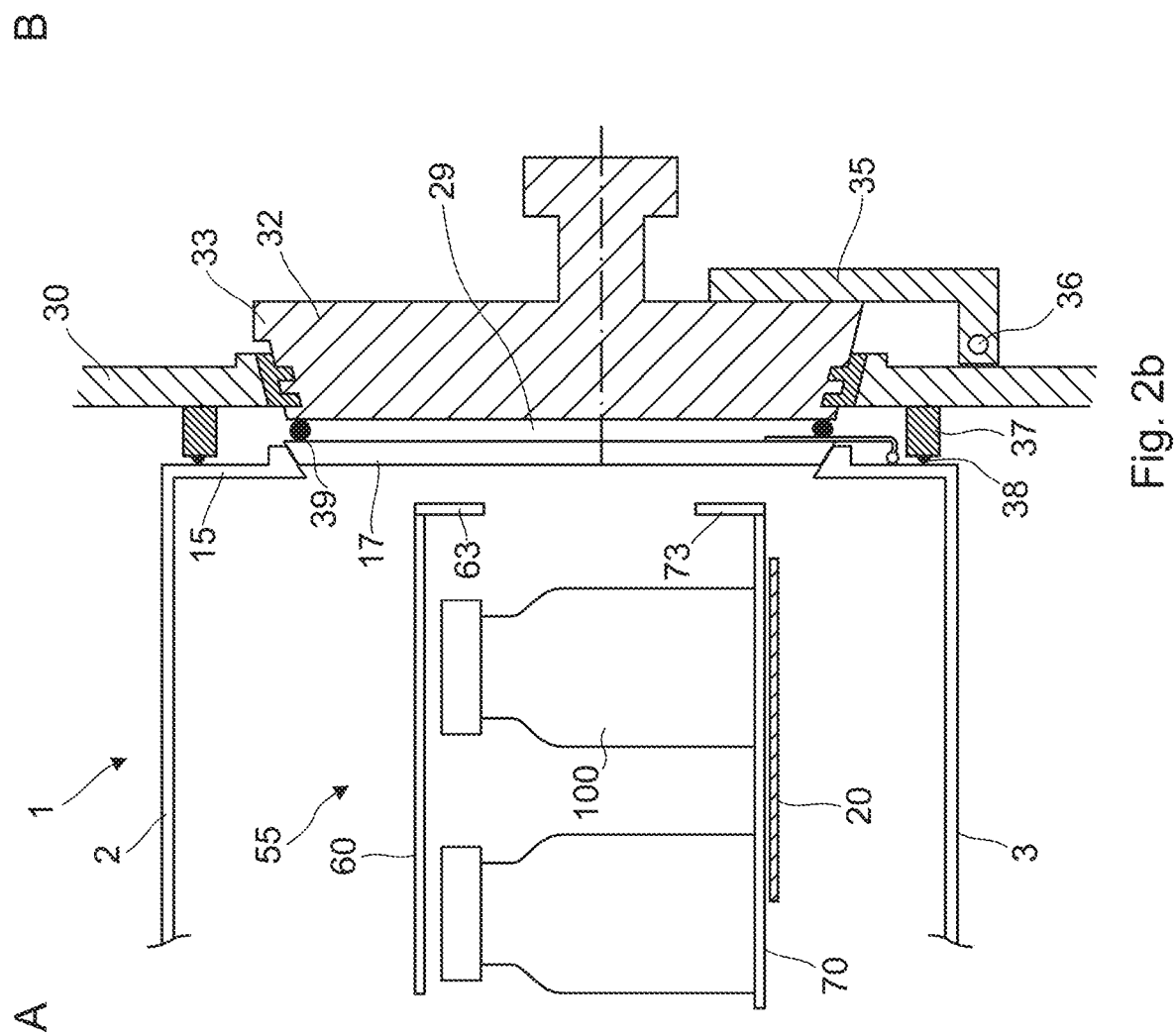

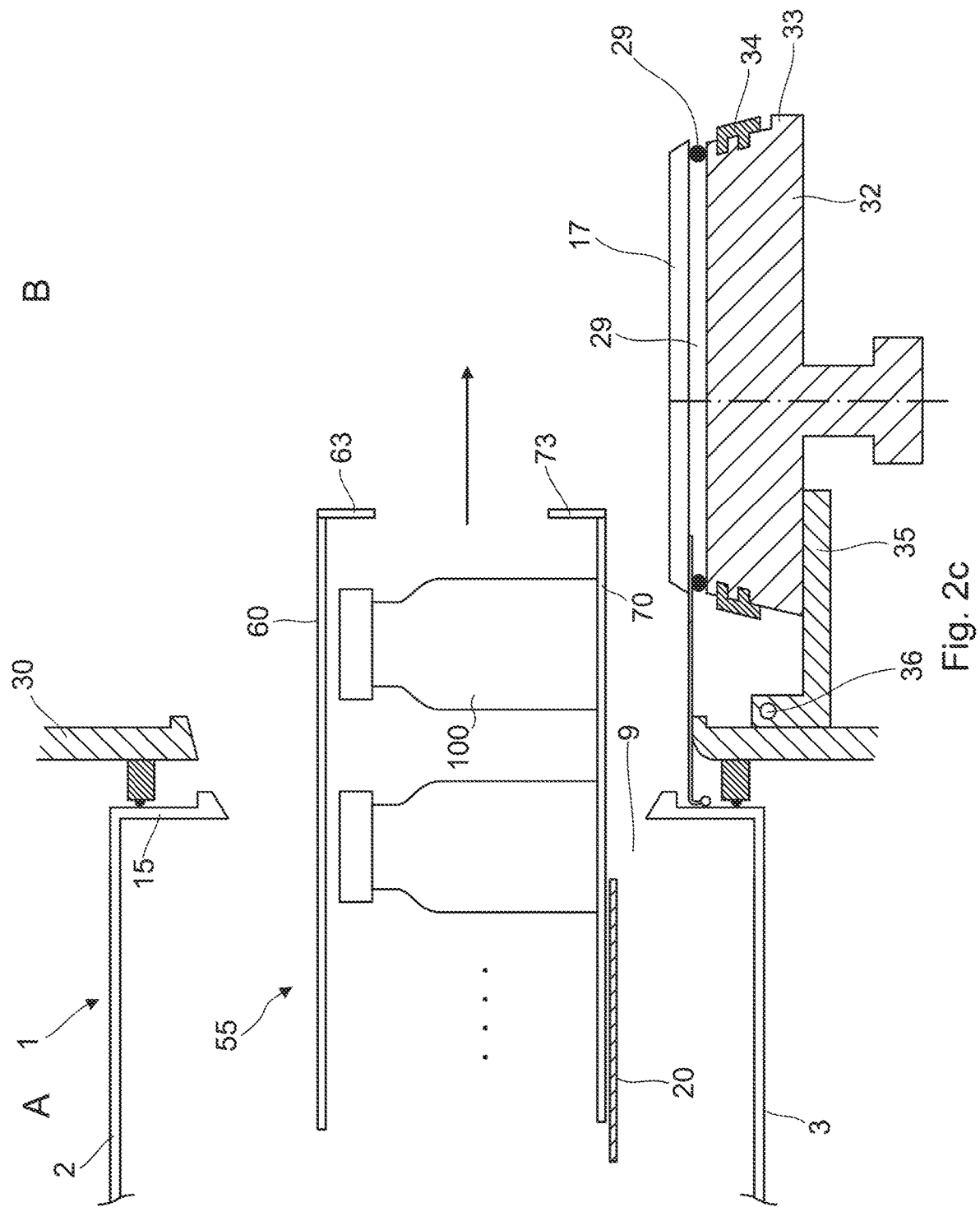

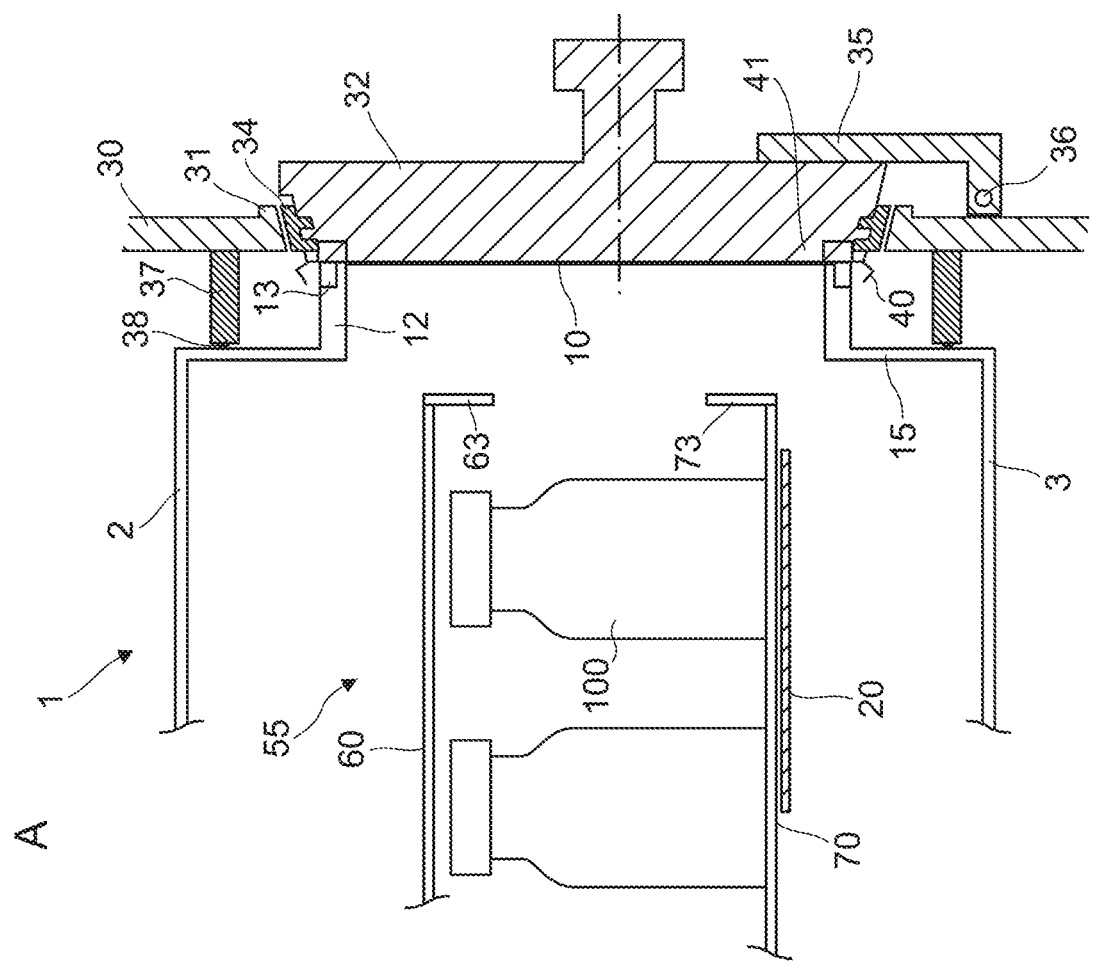

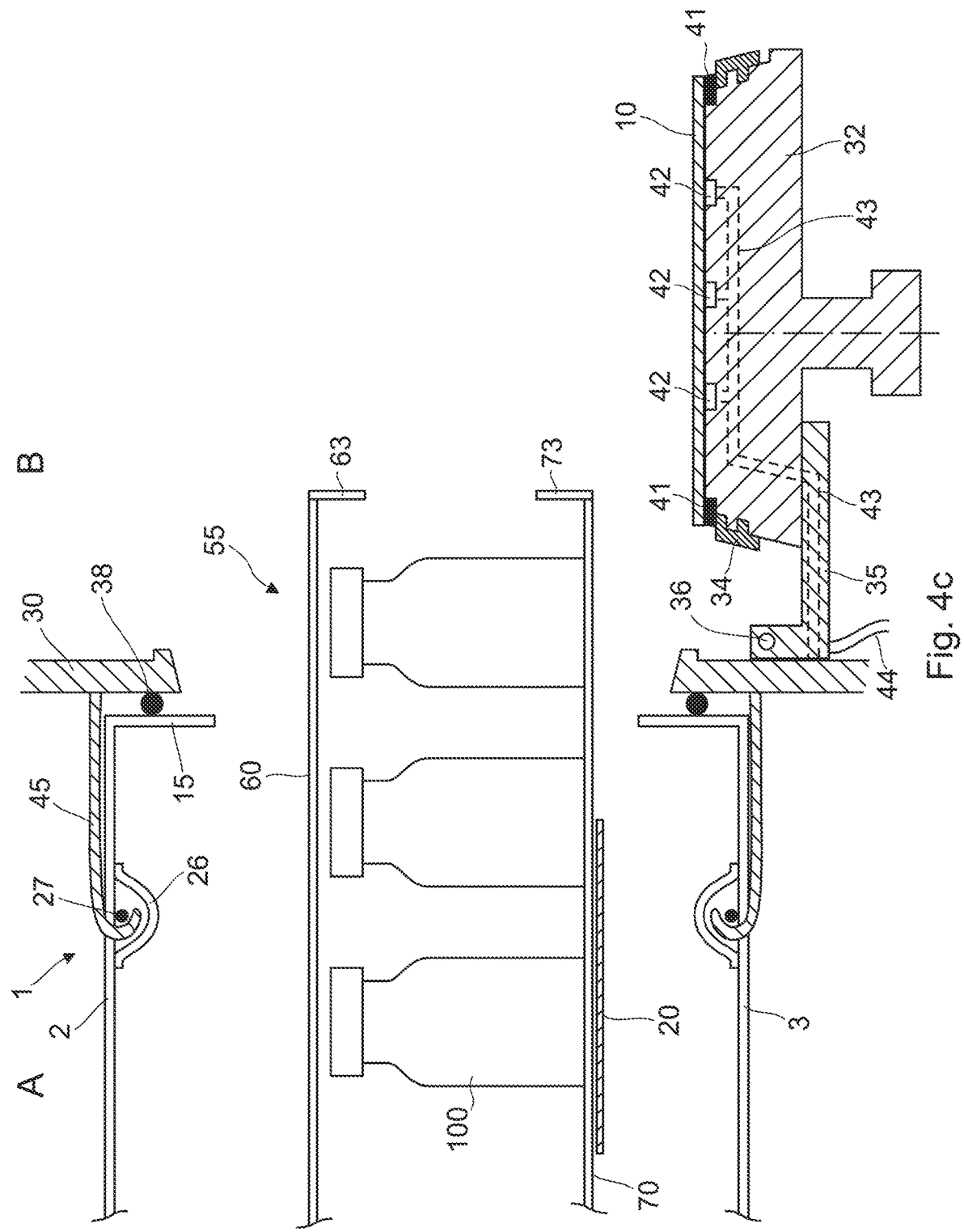

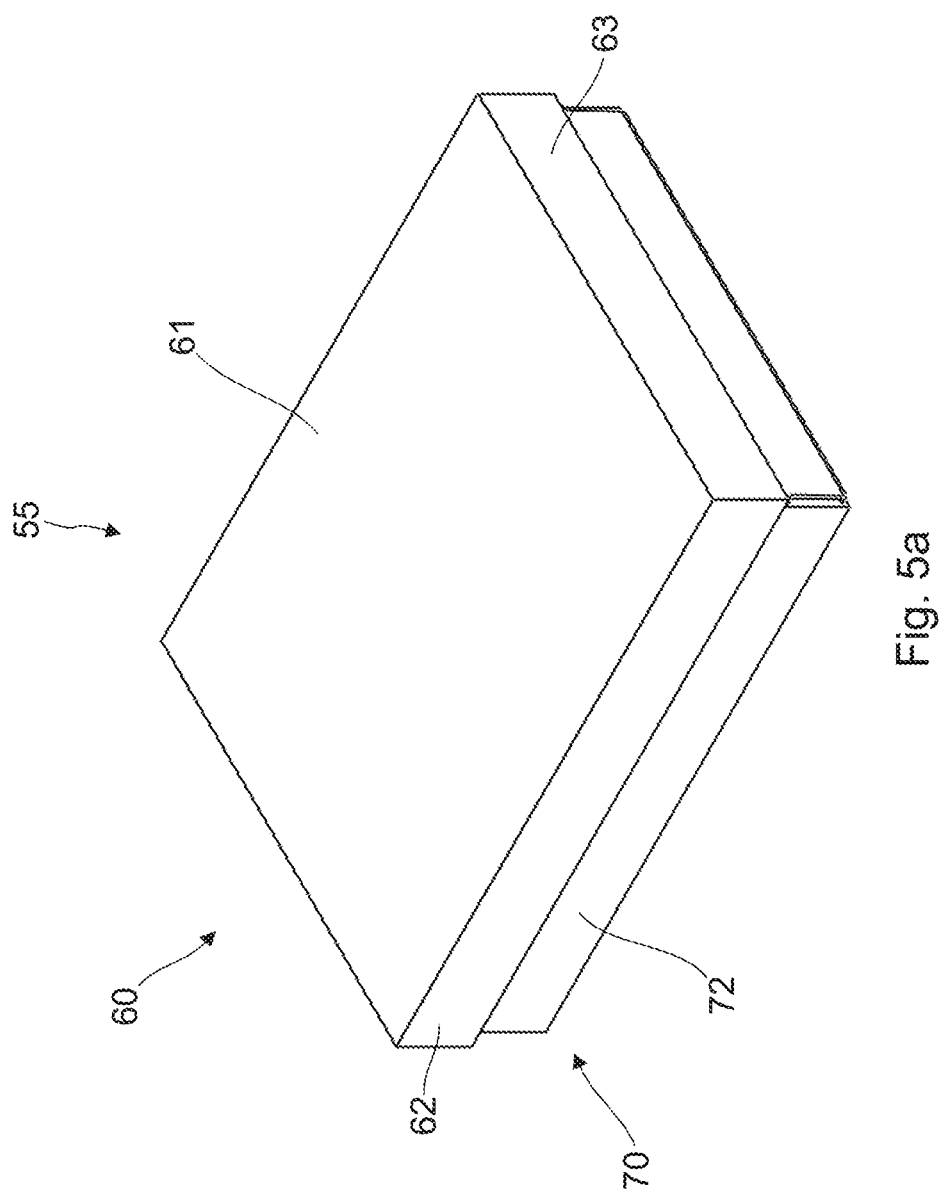

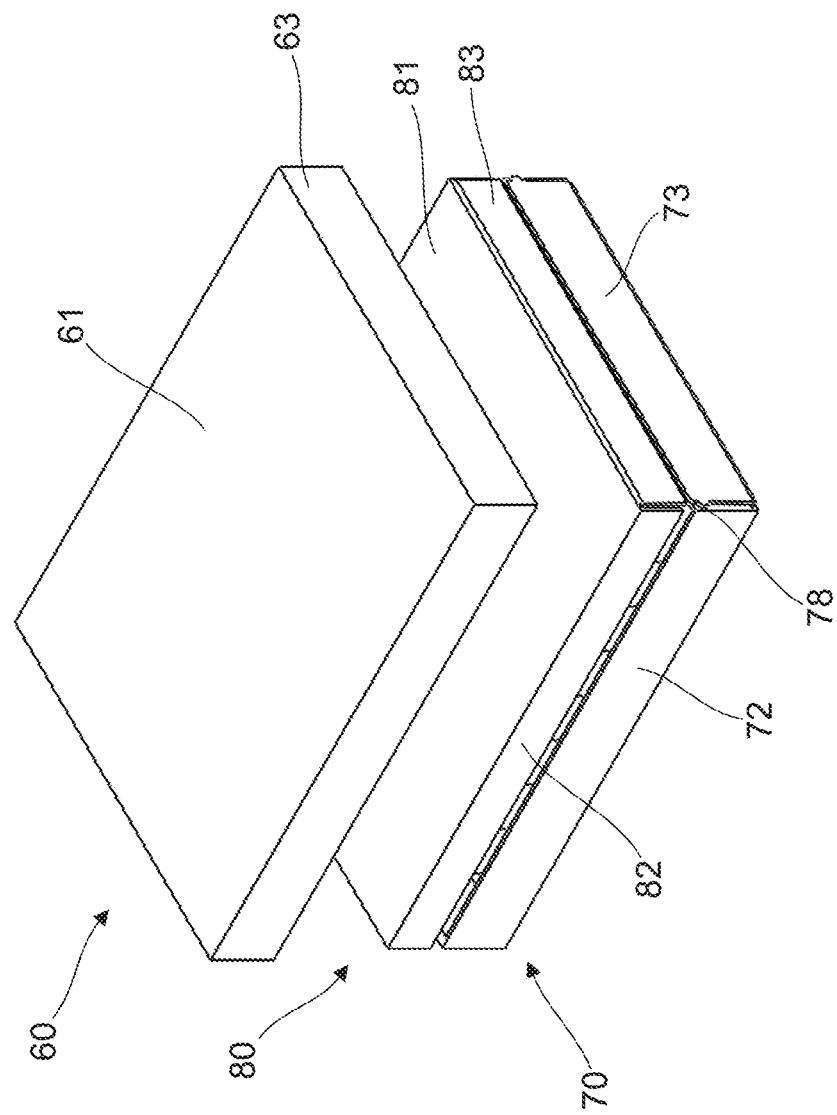

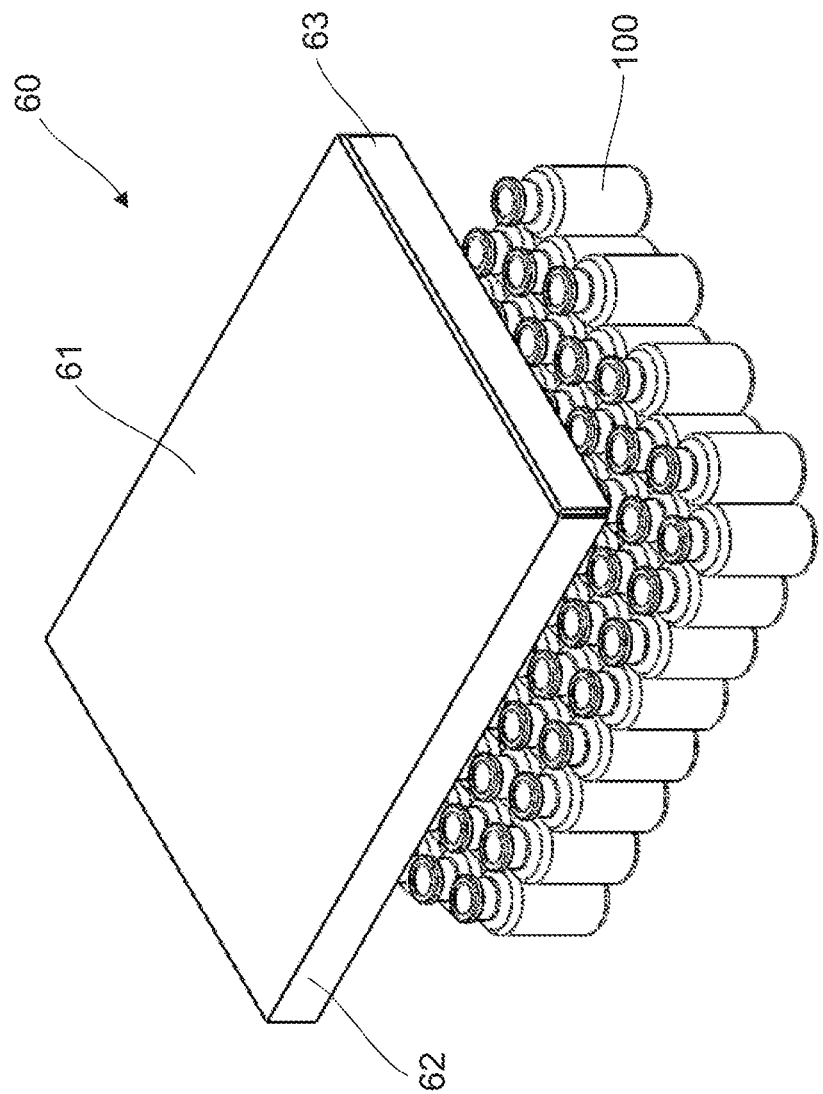

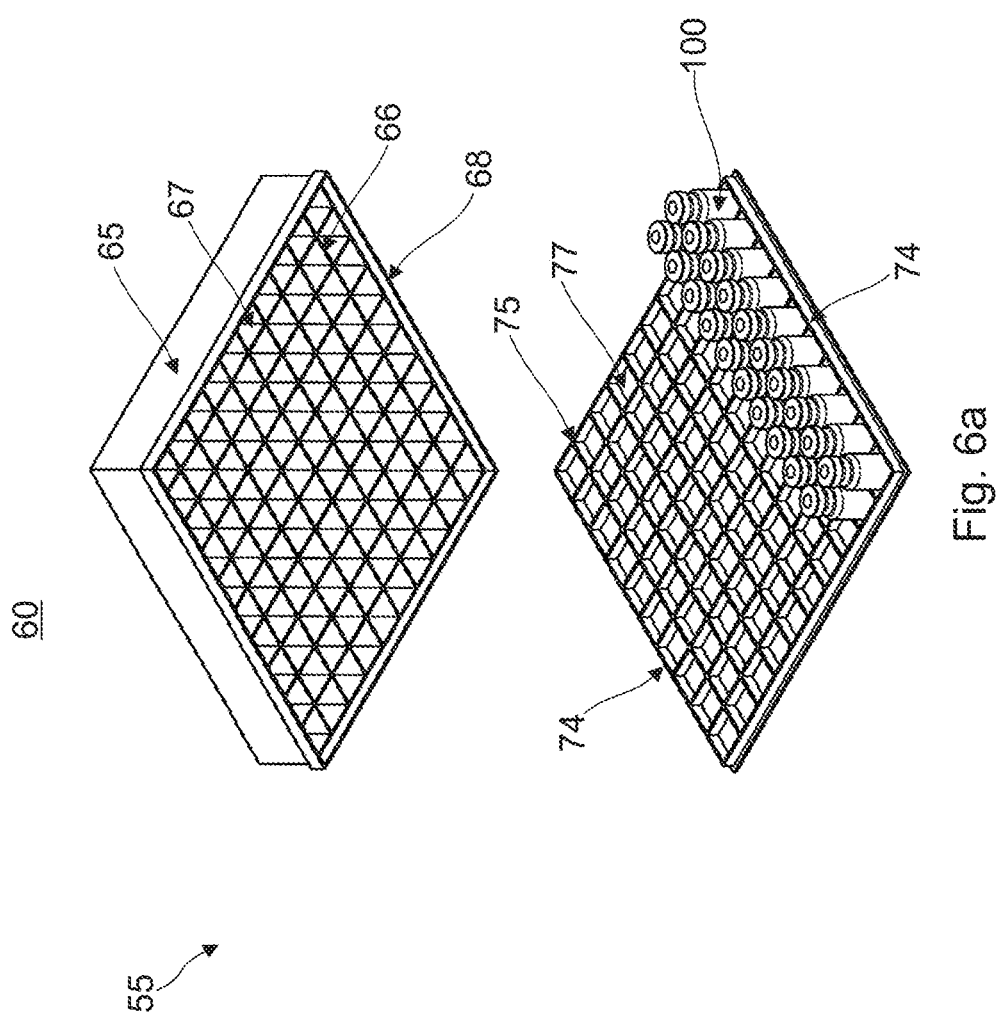

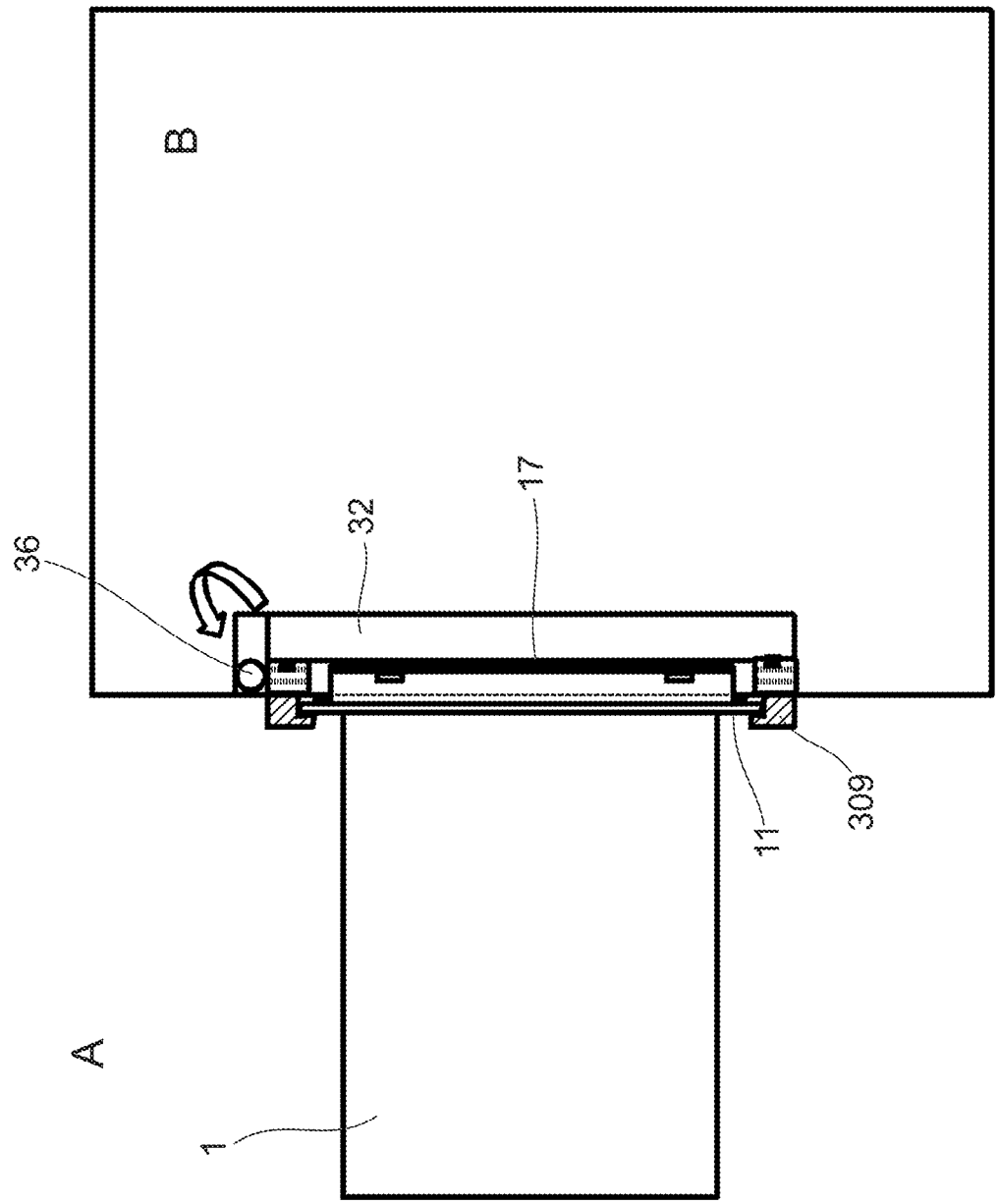

METHOD OF TRANSFERRING A PLURALITY OF CONTAINERS AND/OR CLOSURE ELEMENTS INTO A CLEAN ROOM, TRANSPORT AND PACKAGING CONTAINER AND PACKAGING STRUCTURE THEREFORE

CROSS REFERENCE TO RELATED APPLICATIONS

This application claims benefit under 35 U.S.C. § 119(a) of German Application No. 10 2016 103 404.5 filed Feb. 26, 2016, the entire contents of which are incorporated herein by reference.

BACKGROUND

1. Field of the Invention

The present invention generally relates to a method for transferring a plurality of containers for storage of substances for medical, pharmaceutical or cosmetic purposes and/or closure elements for such containers into a clean room, and further relates to a transport and packaging container and a packaging structure for this purpose and to their use for this purpose.

2. Description of Related Art

Medication containers, such as vials, ampoules, syringes or cartridges, are widely used as containers for the storage of medical, pharmaceutical or cosmetic preparations with administration as a liquid, particularly in pre-dosed quantities, which are produced of plastic or glass and are available at low costs and in large quantities. For enabling a filling or further processing of the containers under sterile conditions as efficiently as possible, concepts are increasingly used, where the containers are sterile packaged in a transport and packaging container or in a packaging unit already by the manufacturer of the containers and are then unpacked at a pharmaceutical company under sterile conditions, in particular in an isolator, in a clean room or in clean room under high purity standards or in an RABS-environment (Restricted Access Barriers Systems), and then further processed.

To this end, the prior art more and more deploys so-called nested packaging concepts, where a plurality of medication containers are first arranged in a supporting structure (also referred to as a 'nest') in a regular arrangement, for example in a matrix arrangement, for transport purposes, because such concepts offer advantages in the automated further processing of containers as the containers can be transferred to processing stations at precisely defined positions and in a predetermined arrangement. For the transport, the supporting structure is then inserted into a transport and packaging container (also referred to as a 'tub'), the upper end of which is sterile sealed using a protective sheet or foil. The transport and packaging container is usually sterile packaged in a packaging bag and it is delivered in this form.

For transferring the medication containers into a clean room, usually transfer ports are used, which are generally known from the handling of radioactive substances. Here, however, also the transport and packaging container needs to be transferred into the clean room. A direct transfer only of the supporting structures together with the medication containers supported thereon into the clean room is not known for nested packaging concepts of the prior art.

US 20150114853 A1 discloses a box-shaped transport and packaging container in which a plurality of containers is supported in a predetermined geometric arrangement. A front side wall of the transport and packaging container can be opened at least partially so that individual containers can be taken out of the transport and packaging container selectively and so that the transport and packaging container can be closed again afterwards. However, specific measures for transferring the containers into a clean room are not disclosed.

EP 2183166 B1 discloses a nested packaging concept. A transport and packaging container which is packaged sterile in a packing bag made of plastic is transferred into a clean room via a transfer port. For the transfer, the packaging bag is temporarily held on the side wall of the clean room around the transfer port of the clean room and the transfer port is only opened afterwards, for preventing the intrusion of particles and germs into the clean room. The transport and packaging container must be transferred into the clean room and can only be opened inside the clean room for a further processing of the medication containers.

US 20090100802 A1 discloses a packaging unit for syringe bodies, comprising a transport and packaging container accommodating a supporting structure at which the syringe bodies are supported. The transport and packaging container is placed inside a packaging bag made of a gas-impermeable plastic, to which a vacuum is applied before sealing the packaging bag by welding which causes that the packaging bag is drawn down into the interspaces between the syringe bodies supported at the supporting structure. For the transfer into a clean room, the outside of the packaging bag must be sterilized, which is costly.

U.S. Pat. No. 8,118,167 B2 discloses a similar transport and packaging container.

The opening of the transport and packaging container and the transfer of the containers or of the supporting structure together with the containers accommodated therein to a process station under sterile conditions is cumbersome, time-consuming, not flexible enough and cannot ensure in any case compliance with high quality standards, in particular for ensuring low concentrations of particles or germs.

For pharmaceutical or medical applications, in most cases the transport and packaging container is packaged according to the 'bag-in-bag'-principle. A packaging produced in a clean room is packaged into a packaging bag, which may also be produced in the clean room. In most cases the packaging itself is packaged two or three times in a packaging bag. The first package (packaging bag no. 1) may become soiled during transport. Then it is transferred through a transfer port into a first room or clean room with a relatively high concentration of particles, where the second package (packaging bag no. 2) is removed until the sterile package finally is transferred into a clean room with a lower concentration of particles, where the further processing of the containers and of the substances to be stored takes place.

WO 95/34078 A1 discloses a method for transferring a plurality of pharmaceutical containers from a loading carriage into a clean room. For this purpose, the door of the carriage is coupled to the door of the clean room and then the door of the clean room is opened. For coupling the door of the carriage to the door of the clean room, however, the door of the carriage must be gas-impermeable.

DE 695 06 008 T2 discloses a corresponding method, wherein two doors are coupled with each other first before the transfer into the clean room. These doors must be impermeable to gas.

DE 696 14 592 T2 discloses that two doors are coupled to each other before the transferring the vials from a carriage into a freeze dryer. These doors must be impermeable to gas.

Further similar methods are disclosed in the documents DE 693 07 433 T2 and US 2005/0042710 A1.

SUMMARY

According to the present invention, there is provided a method for transferring a plurality of containers for the storage of substances for medical, pharmaceutical or cosmetic purposes and/or of closure elements for such containers, which are disposed in a transport and packaging container, into a clean room, wherein the transport and packaging container comprises at least one side wall having an access opening, which is sealed sterile by means of a gas-permeable protective sheet or a gas-permeable lid or cover, comprising the steps of: placing the transport and packaging container together with the plurality of containers and/or of closure elements accommodated therein, so that the side wall of the transport and packaging container is disposed directly at a side wall of the clean room and in close proximity to a transfer port door of the clean room; opening the transfer port door, wherein, by coupling the gas-permeable protective sheet or gas-permeable cover with the transfer port door the gas-permeable protective sheet or gas-permeable cover is separated from the side wall of the transport and packaging container at the same time so that the access opening of the transport and packaging container is in communication with an inside space of the clean room; transferring the plurality of containers and/or the plurality of closure elements from the transport and packaging container into the inside space of the clean room; and closing the transfer port door.

A clean room in the sense of the present invention, into which the containers shall be transferred for the purpose of further processing, is a controlled area with a controlled low concentration of particles or germs, which can be achieved in a known manner by an appropriate air flow and by air filtering. For the transfer, a transfer port door is provided on a side wall of the clean room, in particular a transfer port door which seals and closes an access opening of the clean room and which can be opened in a controlled manner. Such material locks or transfer port doors may have different geometric shapes, for example, these may be circular or rectangular, and these are disposed on the side wall of the clean room in a closed position to provide a sealing effect. For this purpose, a suitable seal, in particular an elastic seal, is disposed extending around the rim of the material lock or transfer port door and/or around the access opening of the clean room. Such transfer port doors can be opened and closed again by means of a pivoting movement or also by means of displacement movements perpendicularly to and/or in parallel with the plane spanned by the side wall of the clean room.

For the transfer into the clean room at a level of intrusion of particles and germs into the clean room that can practically be neglected, it may be generally sufficient to place the side wall of the transport and packaging container at a relatively short distance and in close proximity to the transfer port door or side wall of the clean room, but without contact, particularly if the air pressure inside and outside of the clean room is identical. For example, the width of a gap between the side wall of the transport and packaging container and the transfer port door or the side wall of the clean room is less than about a quarter, more preferably less than about one-eighth and even more preferably less than about one tenth of the maximum width of the transfer port door.

If the opening of the material lock or transfer port door and of the transport and packaging container, the transfer of the containers and the re-closing of the material lock or transfer port door are performed quickly enough, the probability of intrusion of particles and germs into the clean room can be reduced to a low level that may be acceptable. To this end, it is preferable that the material lock or transfer port door and the transport and packaging container are opened simultaneously for transferring the containers and that they are preferably also closed simultaneously, particularly by a simultaneous synchronous pivoting or appropriate vertical and/or horizontal displacement.

According to a further embodiment, the side wall of the transport and packaging container is placed so close to the side wall of the clean room that a gap between the side wall of the transport and packaging container and the side wall of the clean room is sealed by a sealing element. By coupling the gas-permeable protective foil or cover with the transfer port door, the gas-permeable protective foil or cover is separated or pulled off from the side wall of the transport and packaging container while opening the transfer port door, for providing access to the access opening of the transport and packaging container for the transfer of the plurality of containers from the transport and packaging container into the inside space of the clean room.

Because the gap between the side wall of the transport and packaging container and the side wall of the clean room is sealed, an intrusion of particles and germs from the outside of the transport and packaging container into the inside space of the clean room is excluded. If the side wall of the transport and packaging container, which is in contact with the side wall of the clean room, is properly sterilized before—or alternatively after—a temporary coupling of the front side wall of the transport container to the side wall of the clean room or if it was sterile packaged beforehand, e.g. in a sterile plastic bag, the intrusion of particles and germs from this side wall of the transport and packaging container into the inside space of the clean room is also excluded. Even if particles and germs should be present on this side wall of the transport container, their intrusion into the inside space of the clean room is still reliably prevented, because the protective sheet or cover provided on this side wall of the transport and packaging container is coupled with it before the transfer port door is opened. Preferably, for this purpose a gap between this side wall and the outside of the transfer port door continues to be sealed by a sealing member.

For enabling a separation, in particular a pulling-off, of the gas-permeable protective sheet or cover from the side wall upon opening the transfer port door, the force with which the protective sheet or cover is coupled to the transfer port door, needs to be greater than the force with which the protective sheet or cover rests on the side wall of the transport and packaging container, for example is adhered, pressed or latched with the latter.

For this purpose, the coupling may be accomplished particularly by latching, by temporary fixing the protective sheet or cover at the outside of the transfer port door by means of adjustable gripping devices or by suction of the protective sheet or cover against the outside of the transfer port door. To this end, appropriate adjustable or activatable holding or coupling devices are provided on the transfer port door, for temporary coupling of the protective sheet or cover with the transfer port door, which are supplied with energy for the adjustment or activation via the transfer port door itself.

According to a further embodiment, the sealing element is an elastic sealing element and it is disposed on the side wall of the transport and packaging container and/or on the side wall of the clean room. Conveniently, the sealing element is circumferential to provide for the above-mentioned sealing effect at a suitable position, in particular for sealing the gap between the side wall of the transport and packaging container and the side wall of the clean room and/or the gap between the cover and the transfer port door.

According to the invention, the protective sheet or cover of the side wall of the transport and packaging container is gas-permeable, in particular a sterile, gas-permeable protective sheet, particularly a gas-permeable plastic film consisting of a mesh of plastics fibers, for example made of polypropylene fibers. Preferably the gas-permeable protective sheet is a Tyvek®-protective film that is bonded onto a rim of the side wall of the transport and packaging container so that it can be pulled off easily.

According to a further embodiment, the cover may be formed as a lid made of a gas-impermeable material, for example of a plastics material, which is releasably connected in a suitable manner to the side wall of the transport and packaging container, for sterile sealing the access opening. For this purpose, the lid may be latched suitably with the side wall of the transport and packaging container. Preferably, the lid is configured in the manner of a frame, having an opening which is sterile sealed by a gas-permeable protective sheet, as described above. Particularly, this protective sheet may be bonded onto the frame, so that it can be peeled off easily. Basically, this opening may also serve as the access opening to the inside space of the transport and packaging container for removal of the containers and/or closure elements.

According to a further embodiment the method further comprises the step of sterilizing the containers and/or closure elements accommodated in the transport and packaging container by a gas or vapor flowing through the sterile, gas-permeable protective foil or cover. Preferably, this sterilization may be effected via the front and/or rear side wall of the transport and packaging container so that the inside space of a transport and packaging container still can be reliably sterilized, if a plurality of transport and packaging containers is stacked one above the other. If a gas-permeable protective foil or cover is provided on the front and rear end face of the transport and packaging container, as described above, a sterilization may also be effected, for example, via the rear side wall, before the transfer port door is opened to the clean room to reduce the risk of intrusion of particles or germs into the clean room even further.

According to a further embodiment a heating device is disposed at the transfer port door in correspondence with an adhesive rim along which the gas-permeable plastic foil is bonded to the edge of the side wall of the transport and packaging container or to the frame of the cover, wherein the adhesive rim is heated and softened by activating the heating device, and the gas-permeable plastic film is coupled with the transfer port door in such a manner that the gas-permeable plastic film is pulled off from the side wall or cover of the transport and packaging container by opening the transfer port door after the softening of the adhesive rim. For this purpose, it may be sufficient if the strength of the coupling of the protective sheet with the transfer port door is stronger than the remaining, low adhesive force of the protective sheet to the adhesive rim after softening of the adhesive.

According to a further embodiment, the gas-permeable protective sheet is disposed on the side wall of the transport and packaging container or on a frame-like projection formed thereon, wherein a plurality of recesses or depressions is formed in the side wall or in the frame-like projection, and adjustable gripping devices are disposed on the outside of the transfer port door corresponding to the recesses or depressions, wherein the gripping devices are adjusted such that, in a first position of the gripping devices, the transport and packaging container is brought freely to the vicinity of the transfer port door of the clean room, the gripping devices are then adjusted to a second position, in which the gripping devices engage with the corresponding recesses or depressions in the side wall or in the frame-like projection while engaging behind the gas-permeable protective sheet for temporarily fixing the gas-permeable protective sheet at the transfer port door, and wherein the transfer port door is opened in the second position of the gripping devices and the gripping devices are adjusted back to the first position after closing the transfer port door.

According to a further embodiment, the containers and/or closure elements are supported in a supporting structure which is accommodated in the transport and packaging container, wherein the supporting structure together with the containers and/or closure elements supported by it are transferred from the transport and packaging container into the inside space of the clean room by shifting. This enables a rapid transfer of the containers and/or closure elements into the clean room, because all containers and/or closure elements can be transferred at the same time by handling the supporting structure. Such a supporting structure can, in particular, be configured as a nest, as is known from nested packing concepts of the prior art.

The closure elements which are to be transferred into the clean room may be, in particular, plugs, piston plugs or closure caps which are to be used in the clean room.

According to a further embodiment, the supporting structure comprises a box-shaped bottom part having a bottom on which the containers are directly supported, and a box-shaped upper part which rests directly or indirectly on the upper ends of the containers and prevents the intrusion of particles or germs into the supporting structure and in particular into the filling openings at the upper ends of the not yet sealed containers.

According to a further embodiment, the supporting structure is guided on guide rails for the transfer from the transport and packaging container into the inside of the clean room, which is of advantage particularly if the floor of the bottom of the transport and packaging container is not flush with the bottom edge of the access opening on the side wall the transport and packaging container.

According to a preferred further embodiment a bottom edge of the access opening of the transport and the packaging container is flush with the bottom of the transport and packaging container, so that the supporting structure may also be pushed or displaced directly on the bottom of the transport and packaging container for the transfer into the clean room.

According to a further embodiment the transport and packaging container is provided sterile packaged in a sterile packaging bag, and a first space, in particular a first clean room, with a higher concentration of particles is disposed upstream of the clean room, the method further comprising the steps of: sterilizing an outside of the packaging bag in the first space, in particular in the first clean room; and removing the transport and packaging container from the sterile packaging bag after sterilization. Generally, the first room may be a standard working environment, for example, a factory working room of a pharmaceutical filling company where the actual clean room is provided, into which the containers shall be transferred under sterile conditions for their further processing. Generally, however, already this first space may also be a defined space having a controlled environment, particularly a controlled concentration of particles and germs, which is connected with the actual clean room, where the containers are to be further processed, via a material lock.

According to a further embodiment, the plurality of containers is transferred back into the transport and packaging after being processed in the clean room by means of the following steps: placing the transport and packaging container in the first space, in particular in the first clean room, with the higher concentration of particles, so that a side wall of the transport and packaging container is disposed close to a transfer port door of the clean room; simultaneously opening the side wall of the transport and packaging container and of the transfer port door so that the access opening of the transport and packaging container is in communication with the inside space of the clean room; transferring the plurality of containers from the inside space of the clean room into the transport and packaging container; closing the transfer port door; closing the transport and packaging container by means of a cover, in particular effected by the simultaneous closing of the transfer port door; sterilizing the outside of the transport and packaging container in the first space, in particular in the first clean room with the higher concentration of particles; placing the transport and packaging container in a sterile packaging bag after sterilization of the outside; and closing the sterile packaging bag.

According to a further preferred embodiment, the transfer of the containers and/or closure elements into the clean room is performed without lifting the supporting structure out of the transport and packaging container vertically upwards. Rather, the orientation of the supporting structure is retained during the transfer, without the necessity of reversing the supporting structure. The transfer is preferably carried out exclusively by shifting or pushing the supporting structure in a horizontal plane without the necessity of lifting the supporting structure for this purpose. According to further embodiments, this does not preclude that the supporting structure is not raised to a small extent, for example, in order to lift it above a bottom edge of the access opening. In any event, this lifting is substantially negligible compared to a vertical dimension of the containers and/or closure elements, in particular less than about a third, more preferably less than about a quarter of a maximum axial length of the containers and/or closure elements which are to be transferred into the clean room. Therefore, according to the present invention complicated mechanical mechanisms for displacing the supporting structure are not necessary.

According to a further aspect of the present invention, there is provided a transport and packaging container for storage of containers for substances for medical, pharmaceutical or cosmetic purposes and/or of closure elements, in particular for use in a method as outlined above, wherein the transport and packaging container is box-shaped and has an upper side, a bottom side and four side walls, of which respective pairs of side walls are opposite and in parallel with each other and spaced apart, wherein at least one of the side walls is sterile sealed by a cover, and wherein the respective cover can be removed to expose an inside space of the transport and packaging container for removal of the containers accommodated in the transport and packaging container. According to the present invention the cover is gas-permeable, in particular embodied as a gas-permeable protective foil or gas-permeable cover, for enabling a sterilization of the inside space of the transport and packaging container and/or of the containers accommodated therein and/or of the closure members by a flow of gas flowing through the gas-permeable protective sheet or cover.

The afore-mentioned side wall is not the upper side or bottom side of the transport and packaging container, whose surface area substantially corresponds to the footprint of the transport and packaging container in normal use with vertical orientation of the pharmaceutical containers, but is an outside that is perpendicular or substantially perpendicular to the footprint. If the footprint of the transport and packaging container is rectangular, this side wall preferably corresponds to the front or rear side wall of the transport and packaging container, which has a smaller base area than the upper and bottom side of the transport and packaging container.

According to a further embodiment at least one coupling device is provided at the transport and packaging container for temporarily coupling of the transport and packaging container with a side wall of a clean room, wherein the respective coupling device is provided outside of the cover and outside of an access opening of the transport and packaging container.

Mechanical coupling devices such as, for example, depressions, recesses or projections, which may be provided in particular on the front side wall or on the upper and/or bottom side of the transport and packaging container and which can positively engage with adjustable holding claws, are suited for this mechanical coupling. Also adjustable clamping rails or elements of a bayonet mechanism or the like of a suitable design are contemplated. In general, however, the coupling may also be effected hydraulically, pneumatically, electrically or magnetically.

According to a further embodiment, a flat or planar, circumferential abutment portion is formed around the gas-permeable protective sheet or cover, so that a gap between the protective sheet or cover and the side wall of the clean room can be sealed against the environment by an elastic sealing element, if the circumferential abutment portion abuts a correspondingly formed circumferential abutment portion on a side wall of a clean room According to a further embodiment, the sterile, gas-permeable protective sheet is a gas-permeable plastic film consisting of a mesh of plastics fibers, for example made of polypropylene fibers, and preferably the sterile, gas-permeable protective sheet is a Tyvek®-protective film that is bonded on the flat, circumferential abutment portion of the respective side wall of the transport and packaging container. Or the cover is a frame-like lid made of a gas-impermeable material, in particular of a plastic material, having an opening for providing access to the inside space of the transport and packaging container, which is sterile sealed with a gas-permeable protective sheet, as described above, According to a further embodiment, a circumferential rim of the gas-permeable protective sheet is subdivided by a circumferential line-shaped weakened area into an outer circumferential portion and an inner circumferential portion. When the front side of the transport container is coupled with the side wall of the clean room, the outer circumferential portion may be held clamped between the transport container and the side wall, whereas the inner portion of the protective sheet can be pulled off easily along the line-shaped weakened area upon opening the transfer port door of the clean room due to the temporary coupling of the protective sheet to the transfer port door. The weakened area may be formed along the edge of the lid or protective sheet by forming dot-shaped perforations or recesses, for example by punching, deforming, laser ablation or the like. In the case of a protective sheet the line-shaped weakened area conveniently extends within an adhesive rim along which the protective sheet is bonded to the front side of the transport container.

According to a further aspect of the present invention, there is provided a transport and packaging container for containers for the storage of substances for medical, pharmaceutical or cosmetic purposes and/or of closure elements therefore, in particular for use in the afore-mentioned method, wherein the transport and packaging container is of a configuration as disclosed herein and is packaged sterile in a sterile packaging bag.

According to a further aspect of the present invention, there is provided a use of the transport and packaging container as disclosed herein in a method as disclosed herein.

BRIEF DESCRIPTION OF THE DRAWINGS

The invention will now be described by way of example and with reference to the accompanying drawings, from which further features, advantages and objects to be achieved will become apparent. In the drawings FIGS. 1a to 1g show a transport and packaging container according to various embodiments according to the present invention;

FIG. 1h shows a packaging structure comprising a transport and packaging container according to the present invention;

FIGS. 2a to 2d show a method for transferring a plurality of containers from a transport and packaging container into a clean room according to a first embodiment of the present invention;

FIGS. 3a to 3e show a method for transferring a plurality of containers from a transport and packaging container into a clean room according to a further embodiment of the present invention;

FIGS. 4a to 4c show a method for transferring a plurality of containers from a transport and packaging container into a clean room according to a further embodiment of the present invention;

FIGS. 5a to 5e show a supporting structure according to a first embodiment for use in a method according to the present invention;

FIGS. 6a to 6c show details of supporting structures according to further embodiments for use in a method according to the present invention;

FIGS. 8a to 8c show further options for the temporary coupling of a transport and packaging container according to the present invention with the side wall of a clean room.

In the drawings, identical reference numerals designate identical or substantially equivalent elements or groups of elements.

DETAILED DESCRIPTION

Figure 1A:
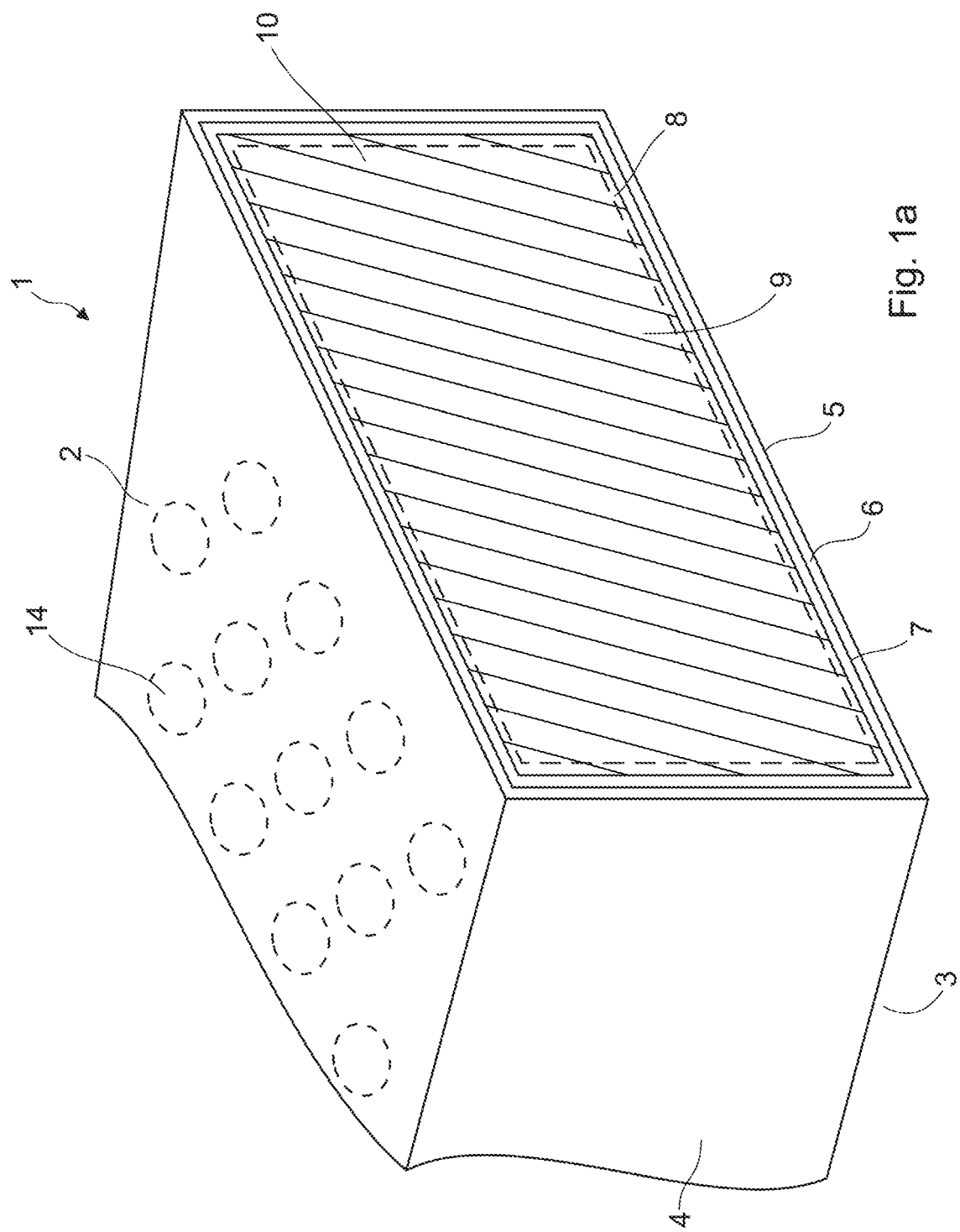

FIG. 1a shows a transport and packaging container 1 (hereinafter also simply referred to as "transport container") according to a first embodiment of the present invention. Overall, the transport container 1 is box-shaped and has an upper side 2, a bottom side 3, two longitudinal sides 4, a front side wall 5 and a rear side wall (not shown). On the front side wall 5, a cover 10 is provided, which sterile covers an access opening 9 to the inside space of the transport container 1. As shown in FIG. 1a, a flat circumferential rim 6 is formed around the edge of the cover 10, wherein the edge of the cover 10 is disposed at a distance to the edge of the front side wall 5. The transport container 1 is conveniently formed of a plastic, in particular by means of an injection molding process, which has a proper stiffness and mechanical stability for mechanically protecting the inside space.

Generally, the cover 10 may be gas-impermeable for sterile sealing the access opening 9. Particularly, the cover 10 may be, for example, a lid of a fully planar design which is releasably coupled with the front side wall 5 of the transport container 1 in a suitable manner to sterile seal the access opening 9. For this purpose, the lid may be screwed or plugged on the front side wall 5 or may be, for example, plugged in the edge of the access opening 9. Of course, the lid 10 may also be bonded on the front side wall 5.

According to a preferred embodiment, the cover 10 is a sterile, gas-permeable protective sheet, in particular a gas-permeable plastic film consisting of a mesh of plastics fibers, for example polypropylene-fibers (PP), and preferably is a Tyvek® protective foil that is bonded along an adhesive rim 8 on the edge 6 on the front side wall 5 of the transport and packaging container 1 by an adhesive agent. Such a protective foil is permeable for a gas (for example, ethylene oxide (ETO) or $H_2O_2$) that may flow through the protective foil into the inside space of the transport container 1 for sterilizing the inside space and the container accommodated therein. If the cover 10 is gas-impermeable, a plurality of openings or perforations 14 may be formed on one of the side surfaces of the transport container 1, in particular on the upper side 2, as shown in FIG. 1a, or also in the cover 10, wherein the openings or perforations 14 are sterile sealed by a sterile, gas-permeable protective sheet, as set-forth above, so that the inside space of the transport container together with the containers accommodated therein may be sterilized by a gas flowing into the inside space through the protective sheet in the region of the openings or perforations 14.

In general it is also possible to sterilize the inside space of the transport container 1 using vapor sterilization using a hot vapor (for example at a temperature of 134° C. and for a duration of 3 minutes) which flows into the inside space of the transport container 1 through the gas-permeable protective sheet.

The aforementioned gas-impermeable lid may be formed like a frame, having an access opening to the inside space of the transport container, which is sterile sealed by means of a gas-permeable protective sheet as described above, which is particularly bonded to the frame.

Figure 8A:
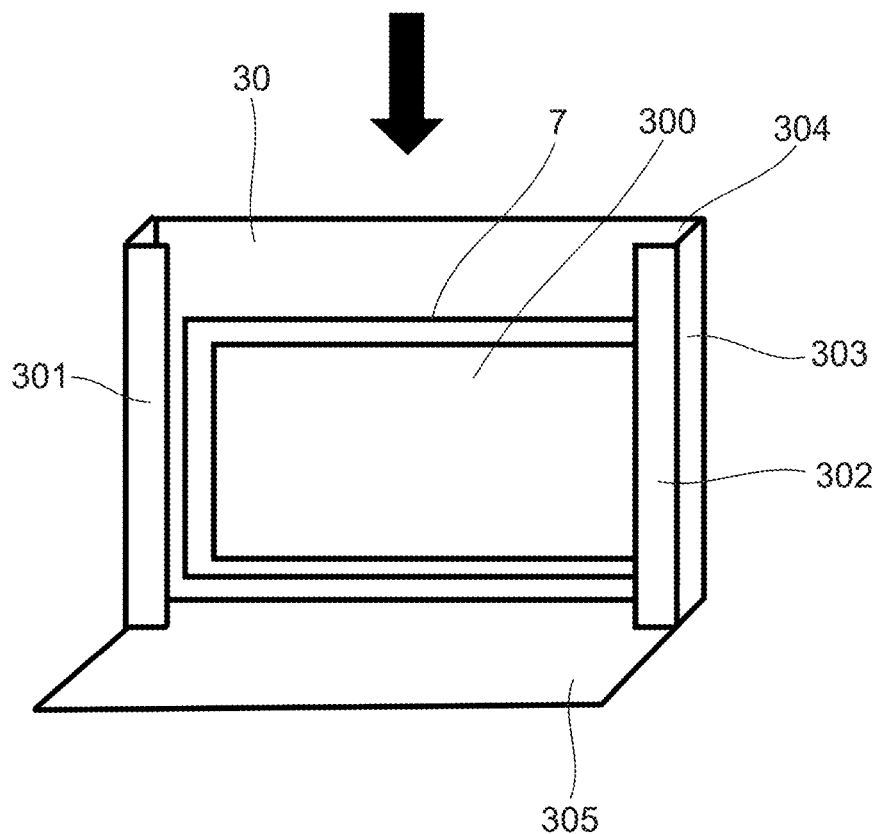
Figure 8B:
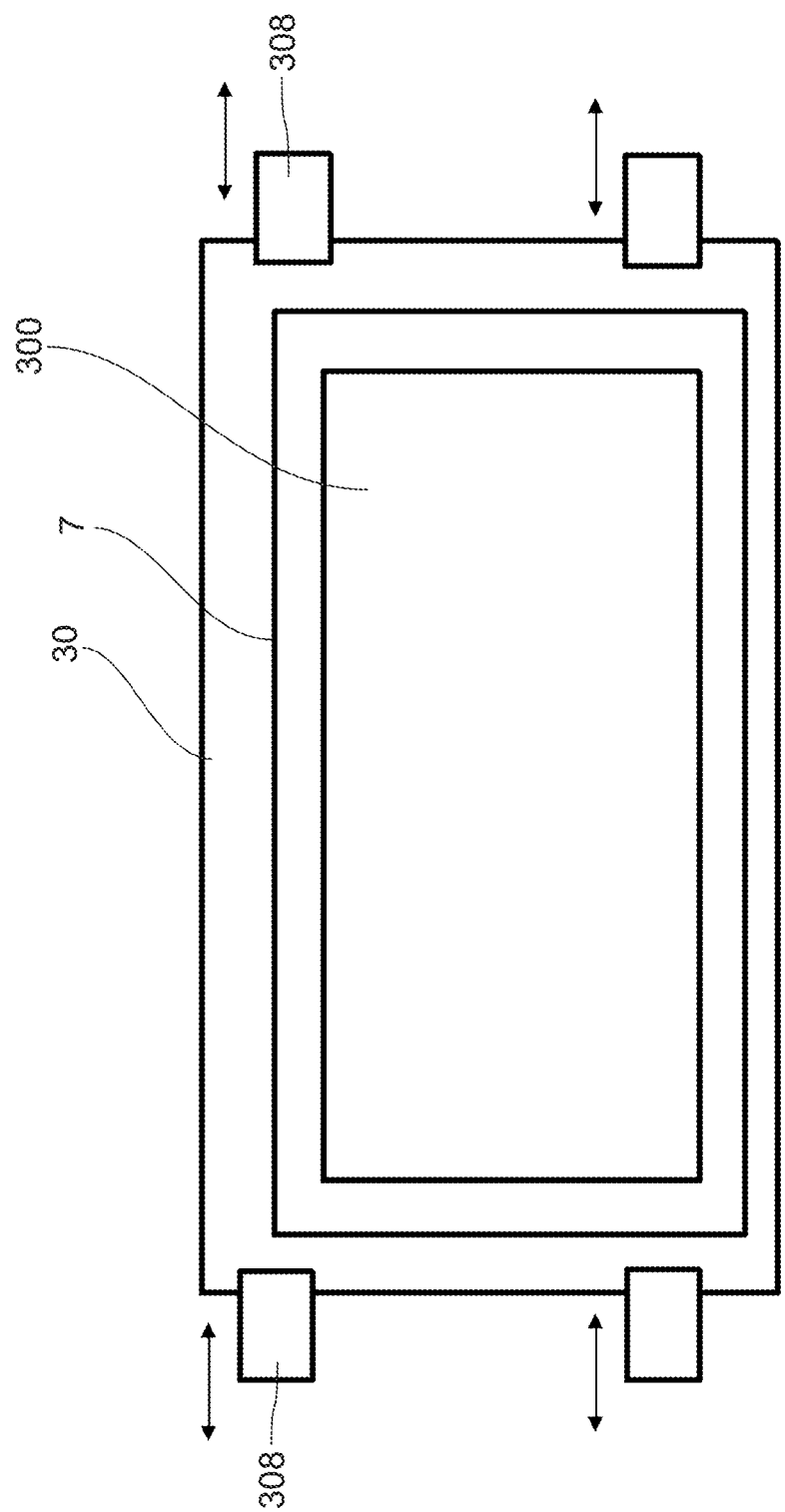

As shown in FIG. 1a, an elastic sealing member 7 is provided on the rim 6, disposed at a distance both to the edge of the front side wall 5 and to the edge of the cover 10, which is for example inserted into a groove provided there or which is formed integrally with the transport container 1 by means of a two-component injection molding technique (2K-injection molding). This sealing member 7 serves to seal a gap 29 (see FIG. 2b) between the transfer port door 32 of a clean room B and the cover 10, as outlined below in more detail. However, its sealing effect may also be replaced by (or performed in combination with) a corresponding seal on the outside of the transfer port door 32, as shown in FIGS. 8*a* and 8*b*.

Figure 1B:
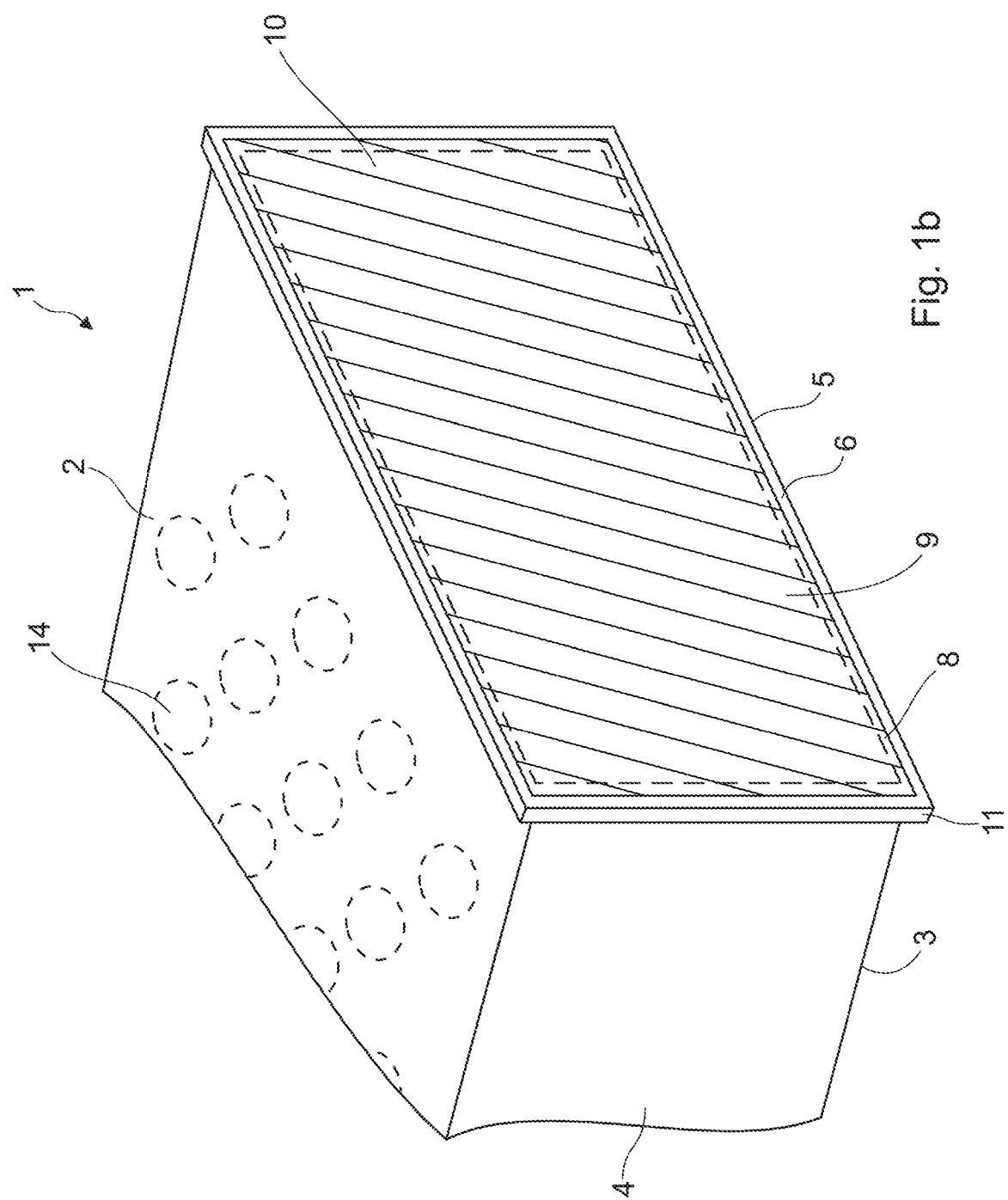

FIG. 1*b* shows a further embodiment of such a transport container 1, wherein the front side wall 5 is widened to a flange 11 that protrudes laterally beyond the bottom side of the transport container 1. Such a flange 11 may be used as a coupling device for temporary coupling the transport container 1 with a side wall 30 of the clean room B (see FIG. 2*b*), particularly if gripping devices or the like grip behind the flange 11, as set-fort below in more detail. Also in this embodiment, a flat, circumferential abutment portion 5 is provided on the front side wall 5, which can seal a gap between the transfer port door of a clean room and the cover 10 by contact with an elastic sealing member on the side wall of a clean room. In this embodiment, the bottom edge of the access opening 9 is preferably flush with the bottom of the transport container 1, so that the supporting structure can be shifted directly on the bottom of the transport container 1 for the transfer into the clean room, as outlined below in more detail.

FIG. 1*c* shows a further embodiment of such a transport container 1, wherein differing from the embodiment of FIG. 1*b* a rectangular, frame-like protrusion 12, which is provided within the rectangular area formed by the elastic seal 7, protrudes from the front side wall 5 on which the cover 10 is provided, in particular a protective sheet bonded to the front side wall 5, as outlined above. As shown in FIG. 1*c*, a plurality of recesses or depressions 13 are formed in the protrusion 12, so that in these areas mechanical gripping devices or the like may grip behind the cover 10 to remove the cover 10, as described hereinafter. Alternatively, such recesses or depressions 13 may also be formed in a corresponding manner along the edge of the flange 11 or of the front side wall 5 of the transport container. 1 Also in this embodiment the bottom edge of the access opening 9 may be flush with the bottom of the transport container 1.

FIG. 1*d* shows a further embodiment wherein in addition to the protrusion 12 a plurality of recesses or depressions 130 is provided, which may serve as coupling devices for the temporary mechanical coupling of the transport container 1 with a side wall 30 of the clean room B (see FIG. 2*b*) so that mechanical gripping devices or the like may grip behind the cover 10 for removal. This is shown schematically in FIG. 8*b*, showing that bolts 308 are provided on the side wall 30 of the clean room at the side of the opening 300 of the clean room that can be adjusted in the direction of the double arrows. In an open position of these bolts 308, the transport container 1 can be brought in close proximity to the side wall 30 until a suitable position is reached, in particular a direct contact of the cover 10 (see FIG. 1*d*) with the transfer port door of the clean room. In this position the bolts 308 are then adjusted inwardly until they engage into the correspondingly formed grooves or recesses 130 on the protrusion 12. Additionally, the bolts 308 may be adjustable in axial direction, in the direction of the side wall 30, for firmly clamping the transport container 1 at the side wall. Also in this embodiment, the bottom edge of the access opening 9 may be flush with the bottom of the transport container 1.

Figure 1F:
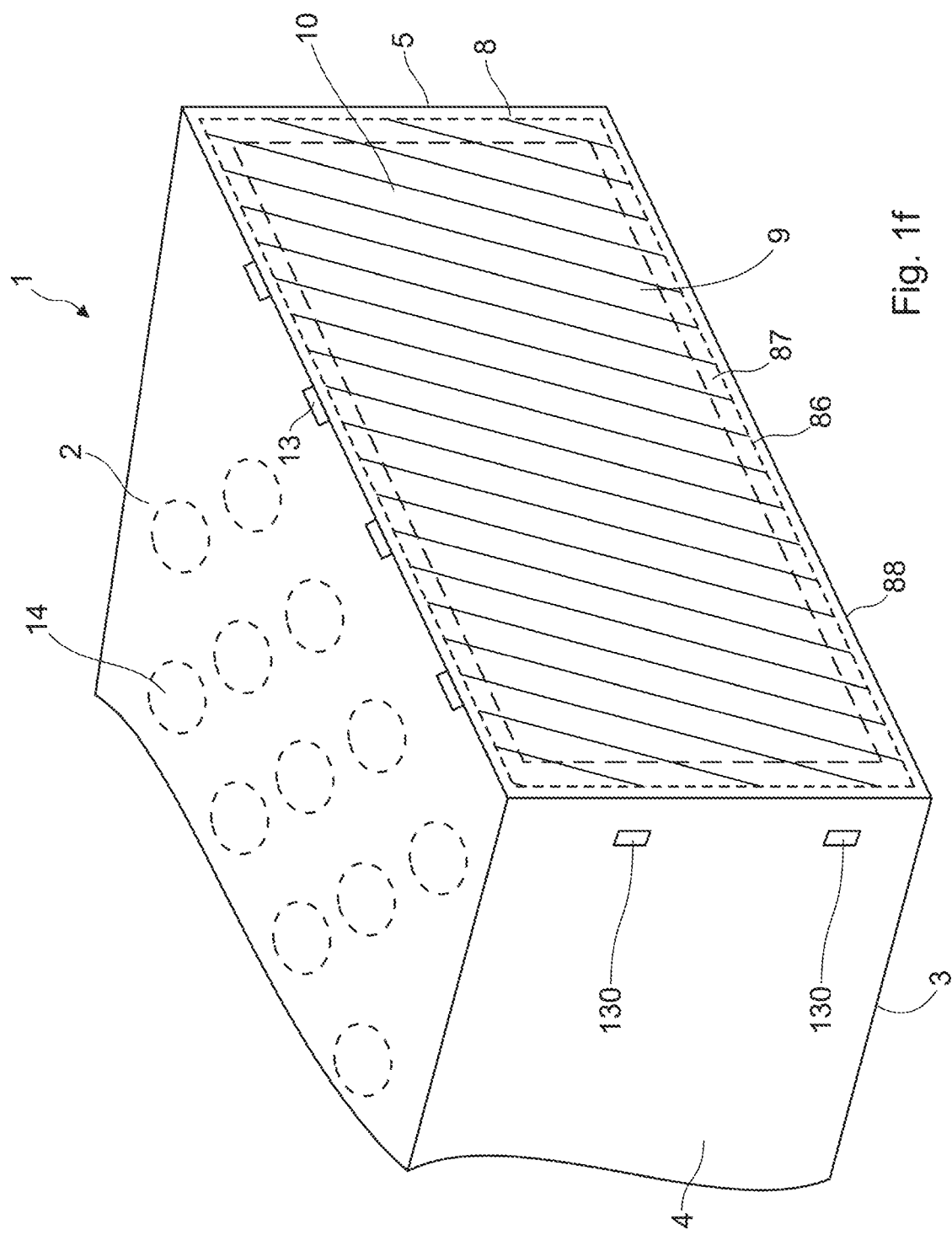
Figure 1G:
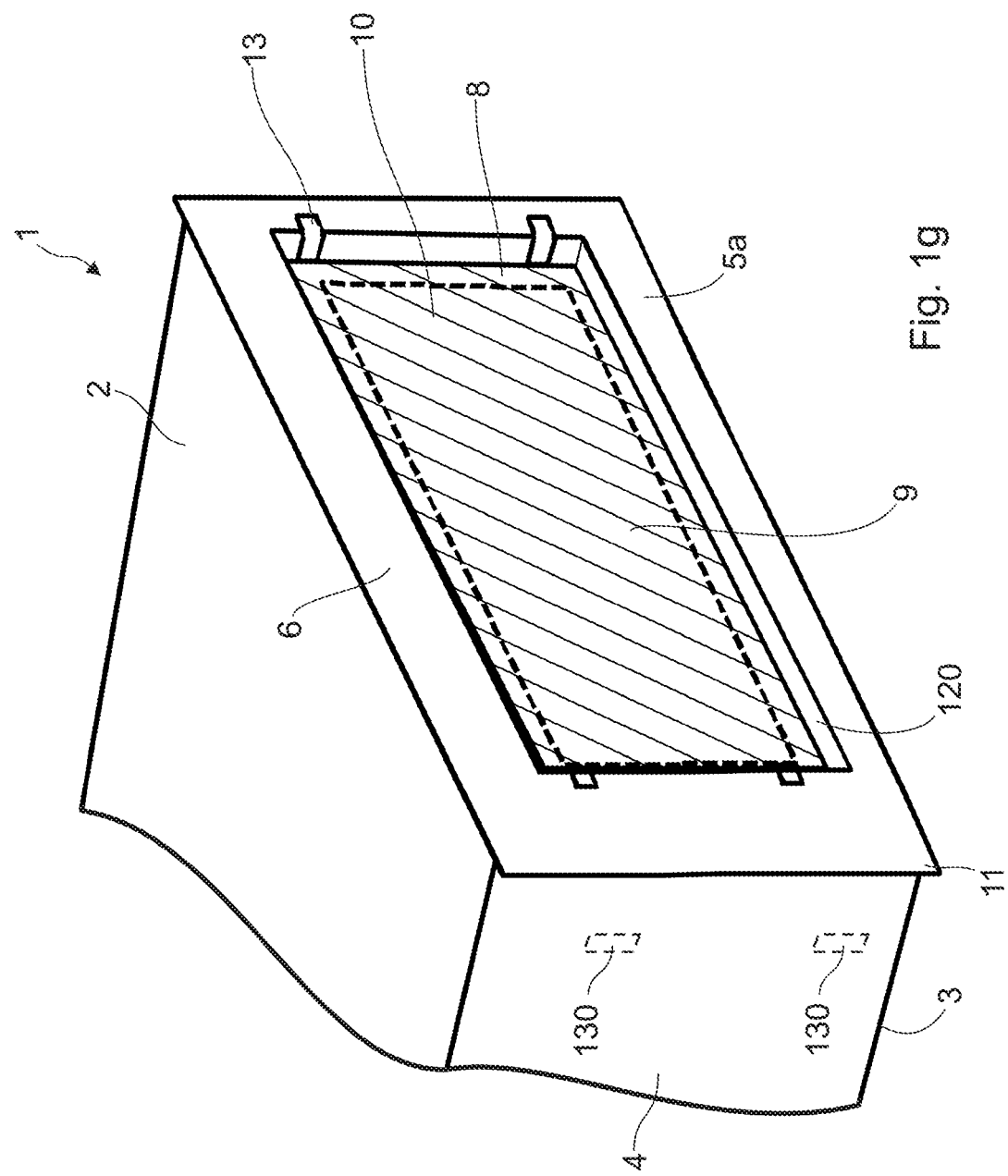

Such recesses or depressions 130 may also be provided on the side wall of the transport container 1, as shown in FIGS. 1*f* and 1*g*. As shown in FIG. 1*f*, the cover 10, in particular a protective sheet as described above, covers the entire front side wall 5 of the transport container 1, without the necessity of aforesaid circumferential abutment portion.

In the embodiment of FIG. 1*e*, additionally an adhesive peripheral reinforcement 85 is provided for the better removal of the cover 10, in particular of a protective sheet. This peripheral reinforcement 85 may be formed as a polymer or as a frame of a plastic or sheet metal and may be adhered by means of an adhesive, which in particular does not need to be configured to be releasable when heat is applied. The removal or tearing-off of the cover 10 from the front side wall 5 is effected in the manner described above by engagement of adjustable gripping devices or the like into the recesses or depressions 13 and by firmly clamping the cover 10, in particular a protective sheet, against the peripheral reinforcement 85, which particularly may prevent an inadvertent rupture of a protective sheet.

FIG. 1*f* shows a further embodiment in which the cover 10, which is in particular formed as a protective sheet, extends up to the edge of the front side wall 5. Here, the cover 10, in particular the protection sheet, is bonded on the front end surfaces of the upper and lower side wall 2, 3 and of the side walls 4 along the adhesive rim 8, wherein the edge region of the cover 10, where it is connected to the adhesive rim 8, is subdivided by a linear weakened area 86 into an outer circumferential portion 88 and an inner circumferential portion 87. By pressing the outer circumferential portion 88 against the side wall of the clean room, the area around the weakened area 86 may be sealed against the environment, particularly if an elastic sealing member is provided in this area (either on the outer circumferential portion 88 of the cover 10 or on the side wall of the clean room) or if the cover itself is resilient to a sufficient extent. The weakened area 86 is configured such that the retaining force exerted by the coupling of the inner portion of the cover 10 to the transfer port door of the clean room is sufficient so that the cover 10 can be pulled off from the front side wall of transport container 1 along the line-shaped weakened area 86 upon opening of the transfer port door, as described below in more detail. Such a weakened area 86 may be formed along the edge of the cover 10 by embossment, by forming a plurality of trough-shaped grooves by laser ablation, laser perforation or the like. Since the cover 10 is still connected with the front end surfaces of the upper and lower side wall 2, 3 and side walls 4 along the inner circumferential portion 87 via the adhesive rim, a sterile packaging can nevertheless be ensured.

Recesses or depressions 130, which serve as coupling devices, are formed in the side wall 4 for temporary coupling of the transport container 1 with the side wall of the clean room, as described hereinafter. Further, a plurality of recesses or depressions 13 is provided in the upper side 2 for pulling off the cover 10, which engage behind both the outer circumferential portion 88 and the inner circumferential portion 87 of the cover 10. A peripheral reinforcement may be provided on the adhesive rim 8, as described above with reference to FIG. 1*e*. In particular it is an advantage of this embodiment that the access opening 9 of the transport container 1 extends up to the bottom 3 and that no disturbing protrusions are the like exist, so that the containers may be supported directly on the bottom of the transport container 1 and may be shifted or pushed through the access opening 9 into the clean room, For the mechanical coupling of such a protective sheet with a transfer port door generally structures that can be handled mechanically, particularly that can be gripped mechanically, may also be provided on the outside of the protective sheet. For example, small dot-like areas of plastic may be fixedly connected to the protective sheet at defined locations on the outside of the protective sheet, for example by lamination or by means of an injection molding process, at which these structures that can be handled mechanically are fixed, for example in the form of annular structures, hooks, eyes or structures having projections and/or recesses, which are made of plastic and which are either formed integrally with the dot-like regions of plastic or secured thereto, for example by gluing or thermal welding.

FIG. 1g shows a further embodiment in which the cover 10 is displaced to the rear with respect to the front side wall 5a by means of a step 120 of a frame-like design. For the temporary mechanical coupling of the transport container 1 with the side wall of the clean room, the flange 11 which projects laterally may be inserted from above into a clamping channel 304 (see FIG. 8a) formed on the side wall 30 of the clean room at the side to the opening 300 of the clean room. The clamping channel 304 shown in FIG. 8a is formed by a front delimiting wall 302 and a side wall 303 of a clamping bar 301, which extends in vertical direction and has a width that is matched to the depth of the flange 11 at the front end of the transport container 1 and allows a sufficient clamping of the transport container 1 in the clamping passage 304. To support the transport container 1 during the transfer of the containers into the clean room, a supporting surface 305 is provided below the opening 300 of the clean room, which also acts as a stop to define the clamping position. Because the cover 10 is displaced to the rear with respect to the front side wall 5a, it cannot be sheared off unintentionally during insertion of the flange 11 into the clamping channel 304.

As will become readily apparent to the person skilled in the art, the afore-mentioned clamping channel may also be designed in a corresponding manner to extend in horizontal direction.

As can be derived from FIG. 1g, a plurality of depressions or recesses 130 is formed in the side wall 4 of the transport container 1 for the optional or alternative coupling, as described above.

For removing the cover 10, in particular the protective sheet, L-shaped recesses 13 are formed in the step 120, the longer leg thereof extending in the longitudinal direction of the transport container 1 and the bottom thereof engaging behind the cover 10, so that adjustable gripping devices provided on the outside of the transfer port door of the clean room can engage behind the cover 10 and clamp it in a suitable manner, as described above.

As will become readily apparent to the person skilled in the art, in all the afore-mentioned embodiments of the transport container the adhesive rim may be subdivided by a line-shaped weakened area into an outer circumferential portion and an inner circumferential portion, for further enhancing a removal of the cover from the front side wall of the transport container by coupling the cover to the transfer port door, wherein the outer circumferential portion continues to be clamped between the transport container and the side wall of the clean room when coupling the cover with the transfer port door.

For a sterile transport of a plurality of containers for medical, pharmaceutical or cosmetic purposes and/or of a plurality of closure elements for such containers, such a transport container 1 is sterile packaged in a packaging bag 58 that may be sealed by welding, as shown in FIG. 1h. For enabling a germ-free transport and a germ-free removal of the containers from the transport container 1, the outside of the transport container 1 is sterilized after insertion of the containers into the transport container 1, in particular before the packing bag 58 is sealed by welding, for example by irradiation, e.g. electron beam irradiation, by exposure to heat, e.g. to a vapor (under controlled conditions), by novel methods, such as oxidative low temperature sterilization, or by chemical agents, in particular by applying a sterilizing gas (e.g. ETO) or a hot vapor. If this has not already been performed beforehand, also the inside of the packaging bag 58 may be sterilized in a suitable manner prior to sealing the packaging bag 58.

As indicated by the arrows in FIG. 1h, also the inside space of the transport container 1, optionally together with the containers and/or closure elements accommodated therein, may be sterilized after sealing the front or rear side wall thereof by means of a vapor, a gas or a chemical agent flowing into the inside space of the transport container 1 through a gas-permeable protective sheet, as described above.

Transport containers (tub) of the aforementioned type are preferably manufactured from a plastic which is sufficiently resistant to deformation and distortion in order to sufficiently protect the containers and/or closure elements accommodated in its interior against mechanical damage. Such a transport container can be produced by injection molding or also by thermoforming a plastic, a square base area being preferred, wherein the height is preferably matched to the height of the containers and/or closure elements to be accommodated. Heights of 3, 4, 5, 6 or 6¾ inches are preferred.

For accommodating pharmaceutical containers, it is preferred if only one layer of pharmaceutical containers is accommodated in the transport container. Conveniently, only one supporting structure with a plurality of pharmaceutical containers and/or closure elements supported thereon is then accommodated in the transport container. However, it general it is contemplated that a plurality of supporting structures are arranged in the longitudinal direction and/or transverse direction of the transport container, for example 3×3 supporting structures or 5×5 supporting structures.

In the transport container, a plurality of supporting structures can, in principle, also be stacked vertically one above the other, which is preferred in particular for the storage and transport of closure elements which are subject to less stringent regulations than pharmaceutical containers. The supporting structures can then be supported in a rack on shelves or else be stacked one above the other, directly or with intervening intermediate layers.

Hereinafter, a process for transferring a plurality of containers from a transport and packaging container into a clean room B according to a first embodiment of the present invention will be described with reference to FIGS. 2a to 2d. Here, it is assumed that the transport container 1 has already been removed from the packaging bag 58, which can take place for example in an additional clean room A having a higher concentration of particles than the clean room B, in which the container shall be processed further afterwards. A method according to the present invention may correspondingly also be used for transferring a plurality of closure elements for pharmaceutical containers, or for transferring a plurality of pharmaceutical containers together with such closure elements.

The supporting structure for the closure elements and the supporting structure for the pharmaceutical containers may be arranged stacked one above the other inside the transport and packaging container, for example in the manner as disclosed in WO 2015/023924 A2. Generally, also exclusively closure elements for pharmaceutical containers may be accommodated in the transport and packaging container, which are supported in a supporting structure in a predetermined array, particularly in a matrix arrangement. The closure elements may be in particular plugs, plunger plugs or caps that shall be used inside the clean room, e.g. for closing the pharmaceutical containers after filling with a drug or liquid.

FIG. 2a shows the conditions after inserting the transport container 1 with the containers 100 accommodated therein into the clean room A, or after opening the packaging bag in the clean room A having the higher particle concentration. In the example shown, the front side wall 15 of the transport container 1 is sealed by means of a gas-impermeable cover 17 having frusto-conical chamfered edges 18 that are inserted into the correspondingly shaped chamfered edge 16 of the front side wall 15 of the transport container 1. The lower end of the cover 17 is coupled with the front connected side wall 15 by means of an elastic tab 19 of an elastically stretchable plastic or rubber material or by means of a suitable fitting that is adjustable in longitudinal direction. An opening may be formed in the gas-impermeable cover 17 which is sterile sealed by means of a gas-permeable protective foil. According to further embodiments, this opening may serve as an access port for transferring the containers and/or closure elements.

The right-hand side of FIG. 2a shows the region of the transfer port door 32 of a clean room B having a lower concentration of particles than clean room A. The transfer port door 32 closes an opening formed in the side wall 30 of clean room B and can be opened by pivoting of the pivot arm 35 together with the associated transfer port door 32 about the pivot axis 36. The transfer port door 32 is frusto-conical and abuts to the correspondingly configured beveled edge 31 of the side wall 30 of the clean room B with the resilient seal 34 interposed. A frame-shaped, circumferential projection 37 is formed around the transfer port door, wherein an elastic seal 38 is provided on its front side wall. According to FIG. 2a a further circumferential resilient seal 39 may optionally be provided on the outside of the transfer port door 32. The transfer port door 32 is intended only as one example of a material transfer port for transferring the containers into the clean room B and can, of course, be replaced by other suitable closure devices, such as those commonly used in the field of pure room technology or clean room technology.

According to FIG. 2a, the front side wall 15 of the transport container 1 is disposed in close proximity to the transfer port door 32 so that the elastic seal 38 on the circumferential projection 37 is disposed opposite to the flat front side wall 15 of the transport container 1 that surrounds the cover 17. In this position, a relatively narrow gap 29 is formed between the front side wall 15 (or cover 17) of the transport container 1 and the side wall 30 (or transfer port door 32) of the clean room B.

In principle, for the transfer of the containers 100 the transport container 1 into the clean room B it may be sufficient according to the present invention, to remove the cover 17 from the front side wall 15 if the gap 29 is sufficiently narrow, for example by lateral removal of the cover 17, and to open the transfer port door 32 simultaneously, for rapidly transferring the containers 100 or the supporting structure 55, in which the containers 100 are supported or accommodated, into the inside space of the clean room B, and then to close the transfer port door 32 of the clean room B quickly again. If this sequence of steps is carried out rapidly enough and the gap 29 is sufficiently narrow, it can be accomplished that the supporting structure 55 or the containers 100 and the inside space of the clean room B are contaminated virtually to a negligible extent when the cover 17 and the transfer port door 32 are opened.

However, according to a preferred embodiment the transfer of the containers 100 from the transport container 1 into the clean room B is performed in the manner, as described below with reference to FIGS. 2b to 2d. According to FIG. 2b, first the front side wall 15 of the transport container 1 is brought into direct abutment with the elastic seal 38, so that the gap 29 between the cover 17 and the transfer port door 32 is sealed against the environment by the circumferential projection 37 and the elastic seal 38 provided thereon. Due to the configuration of the transfer port door 32 and the cover 17 it is ensured in this position that the cover 17 directly abuts the optionally provided elastic circumferential seal 39 on the outside of the transfer port door 32 so that the gap 29 between the cover 17 and the transfer port door 32 is sealed by the circumferential elastic seal 39.

In this position, the cover 17 is temporarily and mechanically coupled to the transfer port door 32, which is not shown in FIG. 2b for reasons of simplicity but which can be implemented easily by latching, by means of gripping devices or by means of a holding or gripping device that may be actuated electrically, magnetically or pneumatically, such as described below with reference to the further embodiments.

After its mechanical coupling with the cover 17, the transfer port door 32 is opened by pivoting the pivoting arm 35 together with the transfer port door 32 attached thereto about the pivot axis 36 into the inside space of the clean room B, whereby the inside space of the transport container 1 communicates with the inside space of the clean room B via the access opening 9. Because of the coupling of the cover 17 with the transfer port door 32, the cover 17 is automatically removed from the front side wall 15 of the transport container 1 when opening the transfer port door 32, whereby access to the access opening of the transport container 1 is provided.

In the opened position of the transfer port door 32 and cover 17 shown in FIG. 2b, the supporting structure 55 together with the containers 100 accommodated therein can be transferred from the transport container 1 into the inside space of clean room B. As shown in FIG. 2c, for this purpose the bottom part 70 of the supporting structure 55 may be displaced or shifted on the guide rail 20, for example on a projection on the inside of the side wall of the transport container 1, as indicated by the arrow in FIG. 2c. Because the inside space of the transport container 1 and the containers 100 have been sterilized before inserting the containers 100 into the transport container 1, for example, by sterilizing with an inflowing gas or vapor, by irradiation or the like, no additional germs or impurities will be introduced into the inside space of clean room B by opening the transfer port door 32 and transferring the containers 100 into the inside space of clean room B. Because the gap 29 between the outside of the cover 10 and the outside of the transfer port door 32 is sealed by the circumferential seal 39 before opening the transfer port door 32, no germs or impurities can be introduced into the inside space of clean room B, neither from the outside of the cover 10 nor from the outside of the transfer port door 32, nor can germs or impurities contaminate the containers 100 when these are transferred into the clean room B in the opened position of FIG. 2c.

Figure 2D:
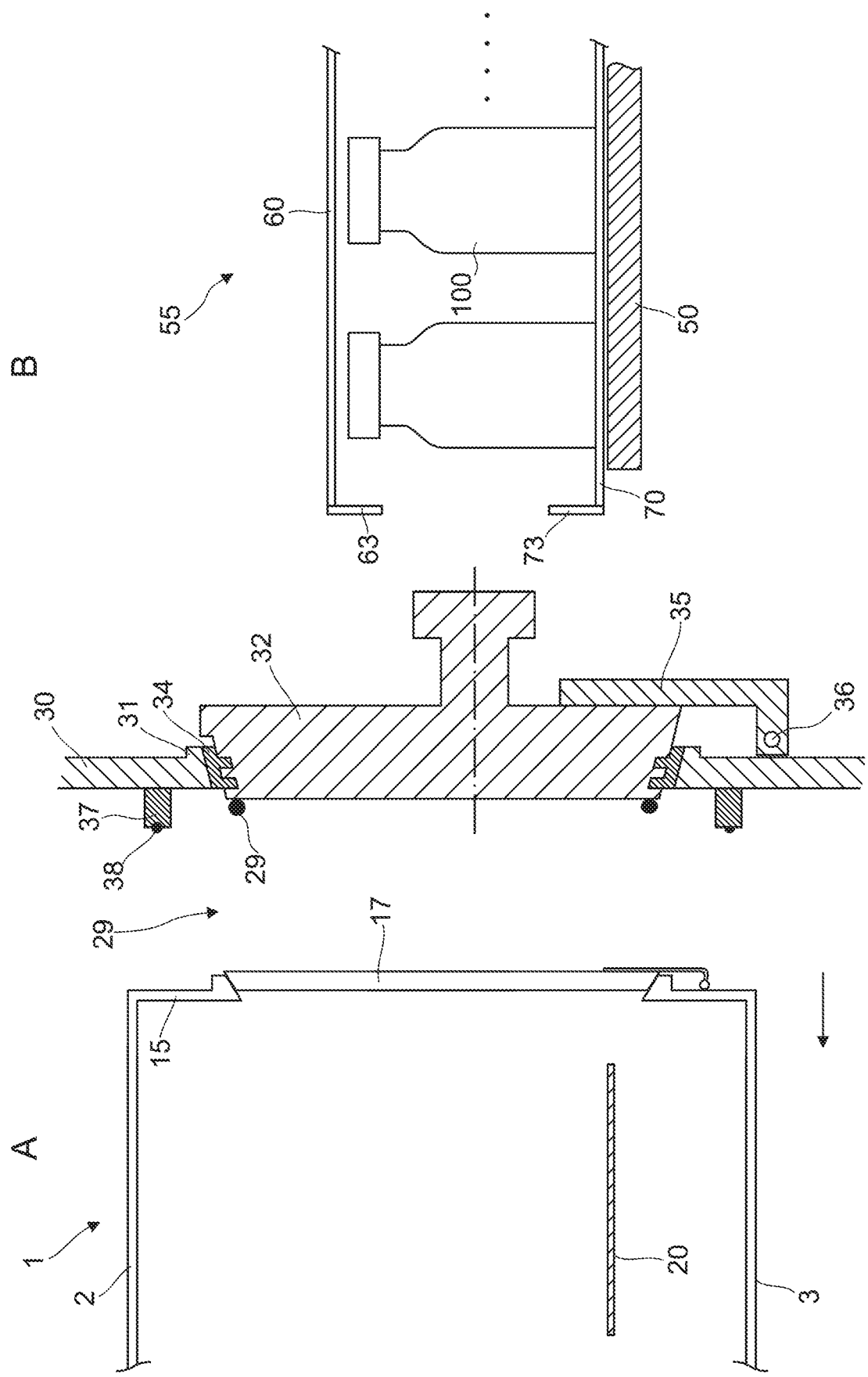

After transferring the supporting structure 55 with the containers 100 accommodated therein from the transport container 1 into the inside space of clean room B, the transfer port door 32 is closed again, as shown in FIG. 2d. Subsequently, the temporary mechanical coupling of the transfer port door 32 with the cover 17 can be released again, so that subsequently the transport container 1 can be with-drawn again from the side wall 30 of clean room B, as shown in FIG. 2*d*, and the transfer port door 32 will thus be ready for the transfer of other containers from a different transport container into clean room B.

Figure 7A:
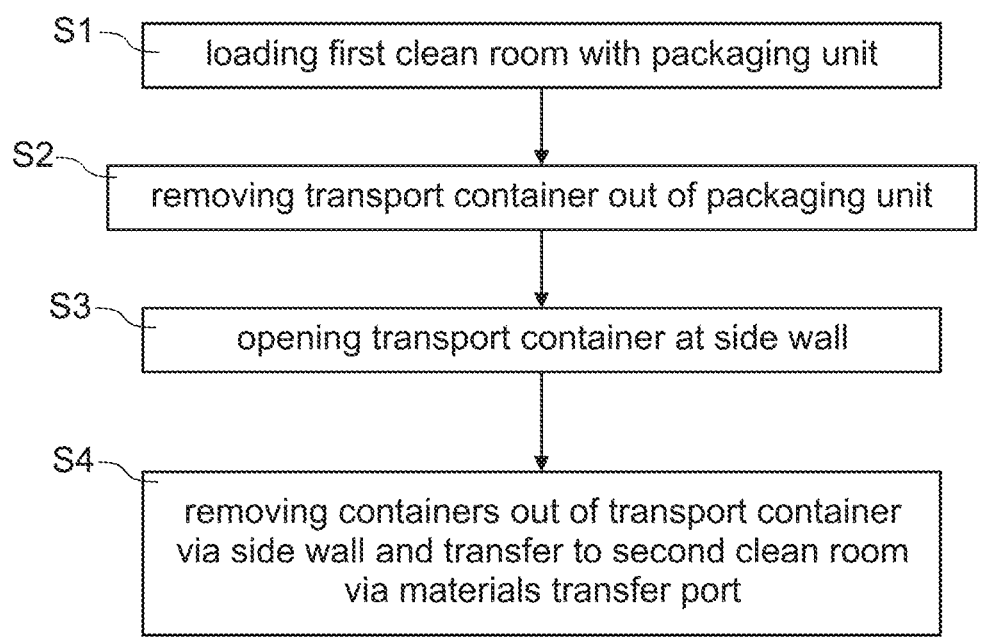
FIG. 7a shows a method for transferring a plurality of containers for the storage of substances for medical, pharmaceutical or cosmetic purposes into a clean room according to a further embodiment of the present invention.

According to FIG. 2*d*, the transport container 1 may be closed again temporarily with the cover 17 and then the cover 17 can be removed again, for example, for accommodating the containers 100 again after their further processing in the clean room B having the lower particle concentration, as will be described below with reference to FIG. 7*c*. In principle, the transport container 1 may, however, also be removed from the clean room A and then disposed or sterilized for a new transport and storage of containers.

While the embodiment shown in FIGS. 2*a*-2*d* was based on the assumption, that the transport container 1 was pressed permanently against the side wall 30 of the clean room B by a force, such as the force of a conveying and adjusting device, in the following a further embodiment will be described with reference to FIGS. 3*a* to 3*e*, wherein the transport container 1 is temporarily fixed or locked on the side wall 30 of clean room B for transferring the supporting structure 55 with the containers 100 accommodated therein from the transport container 1 into the inside space of the clean room B.

Figure 3A:
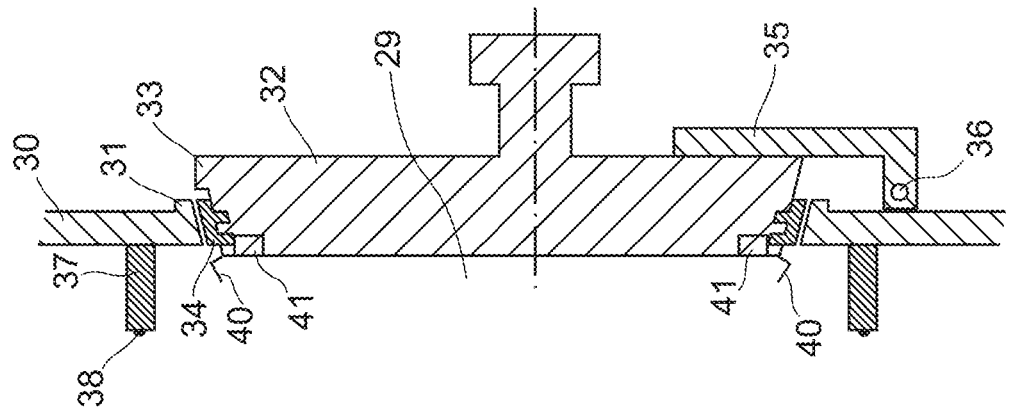
Figure 3A:
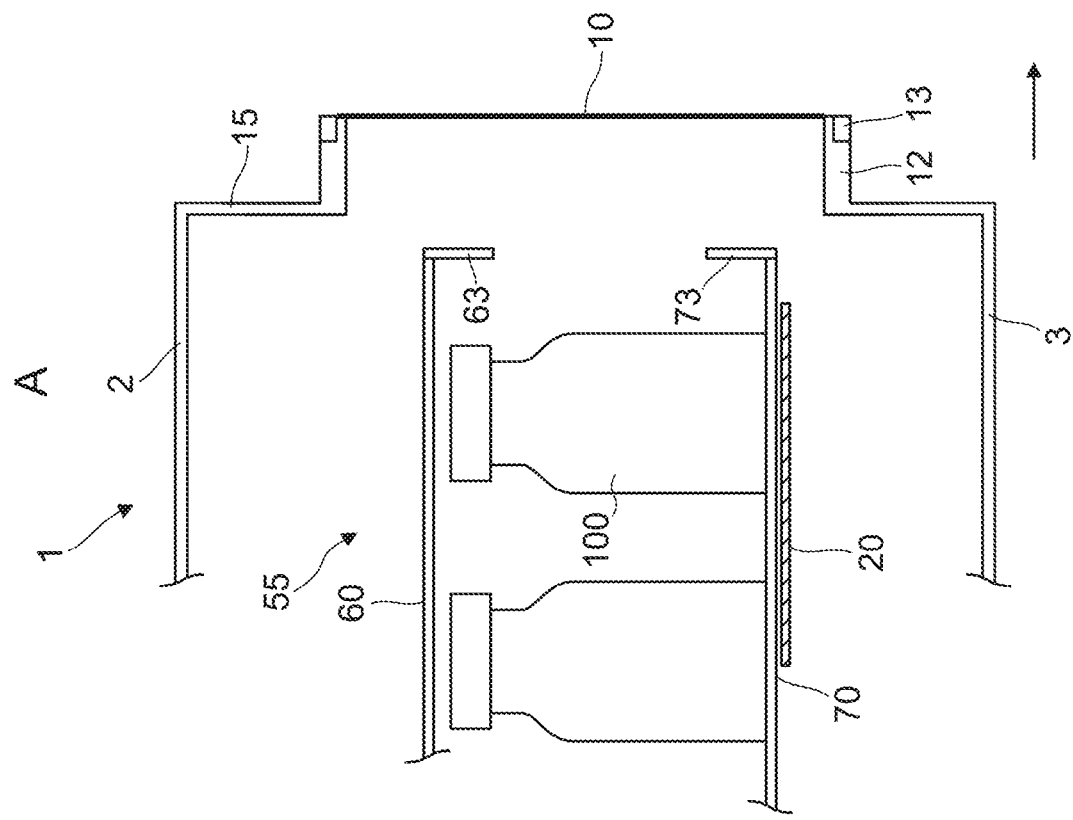

Accordingly, the embodiment of FIGS. 3*a* to 3*e* to be described in the following relies on the use of a transport container according to any of FIGS. 1*c* to 1*e*, where a rectangular, frame-like protrusion 12 is provided on the front side wall 5, on which a gas-permeable protective foil 10 is provided. Generally, however, also transport containers of a different configuration can be used in a corresponding manner. As can be derived from FIGS. 3*a* and 3*b*, adjustable holding arms 40 for temporarily fixing the protective sheet 10 or cover on the outside of the transfer port door 32 are provided on the outside of the transfer port door 32. Referring to FIGS. 3*a* and 3*b*, these holding arms 40 initially are in an opened position in which they do not yet cooperate with the recesses 13 in the frame-like protrusion 12 of the transport container 1.

Starting from the position shown in FIG. 3*a*, the transport container 1 is brought in proximity to the side wall 30 in the opened position of the holding arms 40, until the position shown in FIG. 3*b* is reached, in which the front side wall 15 of the transport container abuts the sealing member 38 on the circumferential projection 37 and the protective sheet 10 is in close proximity to the transfer port door 32 or is in direct contact with the transfer port door 32. In this position, the transport container 1 is temporarily coupled, e.g. locked, with the side wall 30 of clean room B, for temporarily fixing it on the side wall 30. For this purpose, for example, the bolts 308 of FIG. 8*b* can be adjusted inwardly to engage with associated depressions or recesses 130 on the frame-like protrusion 12 (see FIG. 1*d* or FIG. 1*e*) or on the side wall 4 of the transport container 1 (see FIG. 1*f*). The temporary coupling of the transport container 1 with the side wall 30 may also be accomplished by any other type of form-fitting elements, or may be accomplished pneumatically, electrically or magnetically.

Figure 3C:
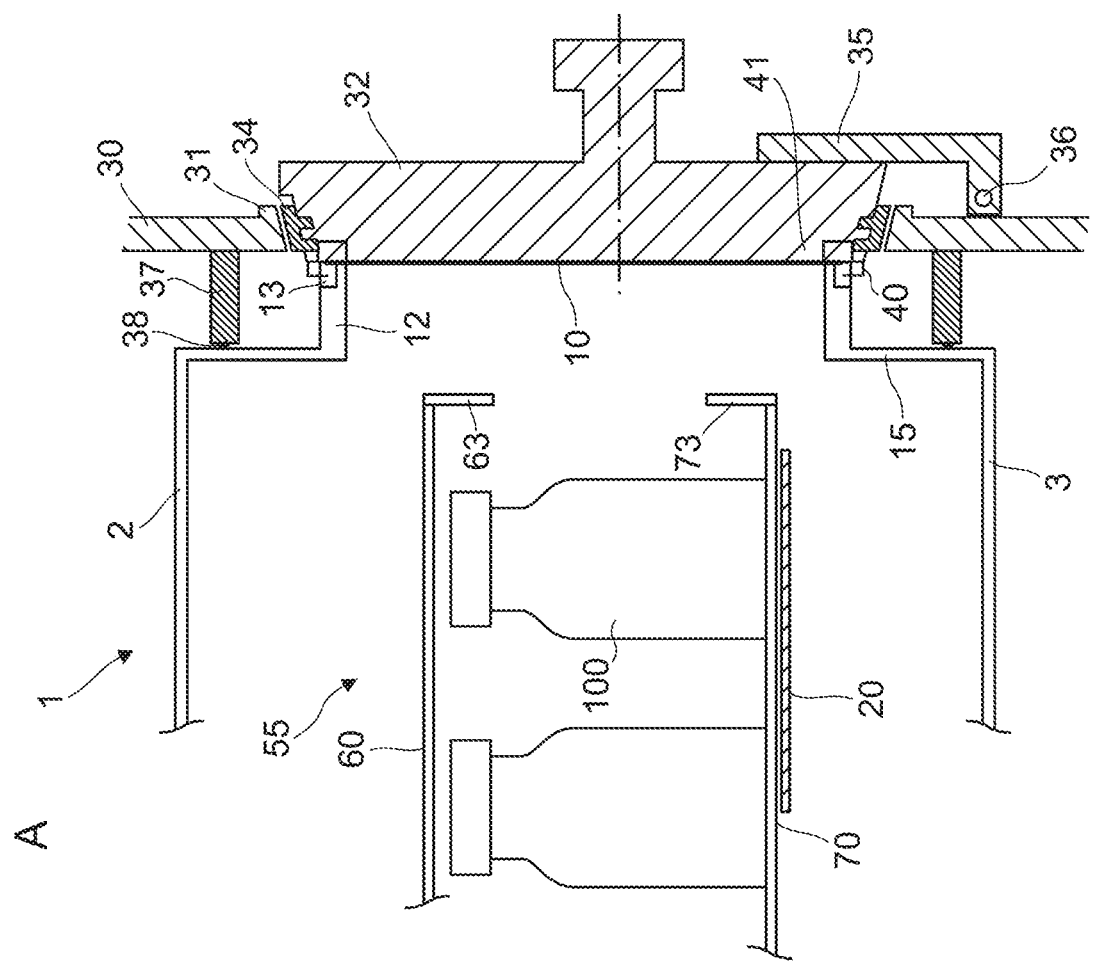

In a next step, according to FIG. 3*c* the holding arms 40 are displaced inwardly, as indicated by the arrows in FIG. 3*c* until they engage with the recesses 13 in the frame-like protrusion 12 of the transport container 1 and thus grip behind the protective sheet 10 or cover, for temporarily fixing the protective sheet 10 or cover at the outside of the transfer port door 32. Here, the protective sheet 10 or cover particularly can be pushed or pulled against the outside of the transfer port door with full-surface contact, or a resilient seal similar to the seal 39 of FIG. 2*a* may be provided between the protective sheet 10 or cover and the outside of the transfer port door 32 for sealing a gap between the protective sheet 10 or cover and the outside of the transfer port door 32. In this position a gap 29 only remains between the front side wall 15 of the transport container and the outside of the transfer port door 32 or of the side wall 30, which is sealed against the environment by means of the circumferential projection 37 and the seal 38 provided on it, for preventing an intrusion of germs in this region.

Figure 3D:
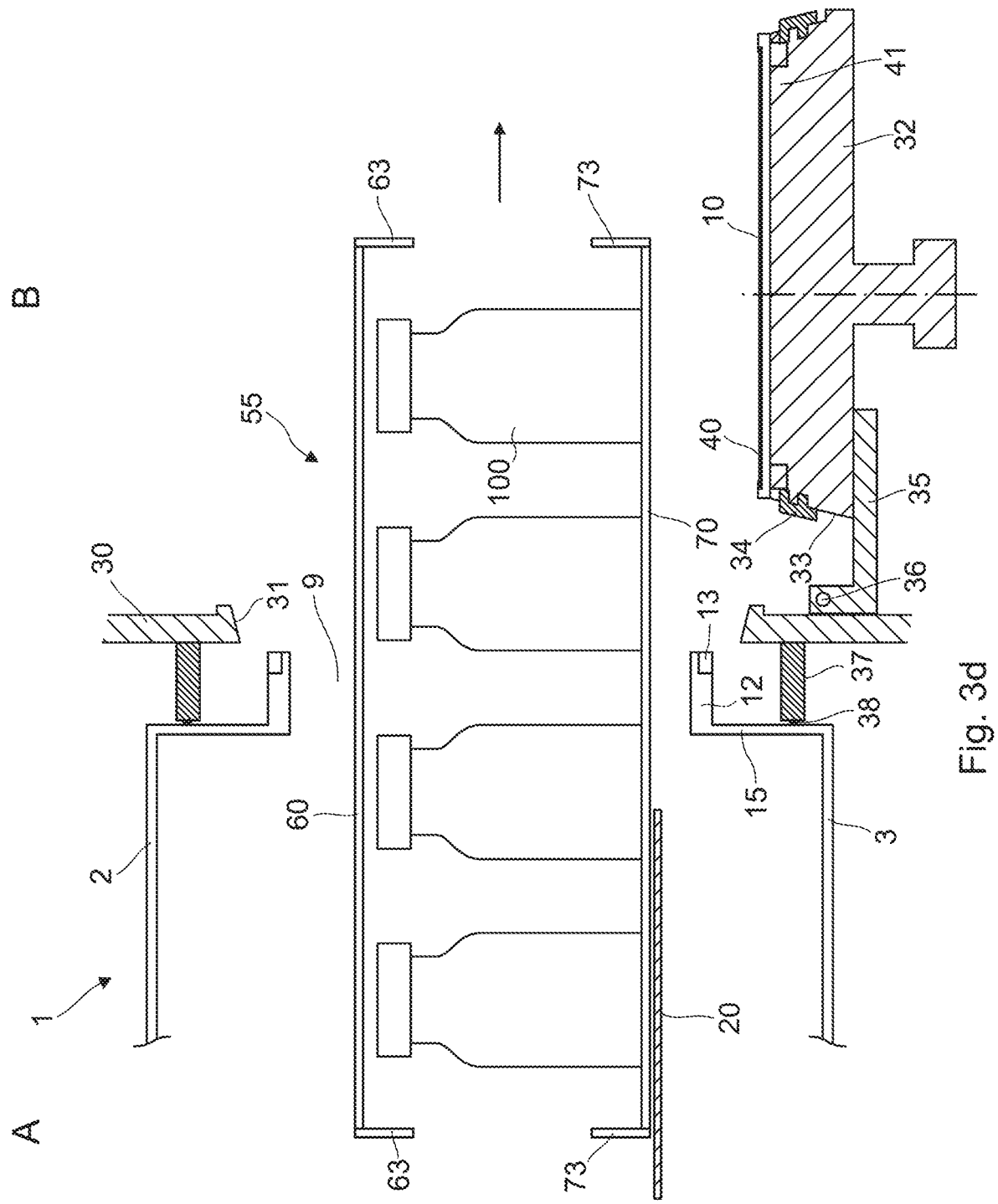

In this position, the transfer port door 32 is opened in a next step, as shown in FIG. 3*d*, so that the inside space of the container 1 then communicates with the inside space of the clean room B via the access opening 9. In this position, the supporting structure 55 can then be transferred into the clean room B by displacement along the guide rail 20. Because the inside space of the transport container 1 has been sterilized when packaging the containers 100, no further germs and impurities can be introduced into the clean room B in this position.

In this embodiment, the protective sheet 10 or cover can be pulled from the frame-like protrusion 12 of the transport container 1 by opening the transfer port door 32, if the holding or clamping force exerted by the holding arms 40 on the outside of the transfer port door 32 is sufficient for this purpose.

When the protective sheet 10 or cover is adhesively bonded to the frame-like protrusion 12 by means of an adhesive, this removal can be further assisted by applying heat and softening of the adhesive caused as a result of this heating. For this purpose, according to FIG. 3*c*, a heating device 41, for example, an electrical heating device, may be provided on the outside of the transfer port door 32 at a position corresponding to the position of the adhesive rim 8 on the frame-like protrusion 12 (see FIG. 1*a*), which is preferably formed circumferential and in correspondence to the opposite adhesive rim 8 on the front side wall 15 of the transport container 1. After activating the heating device 41, the adhesive rim 8 is softened properly, so that the protective sheet 10 or cover temporarily fixed at the transfer port door 32 is pulled off easily from the frame-like protrusion 12 when the transfer port door 32 is opened.

Figure 3E:
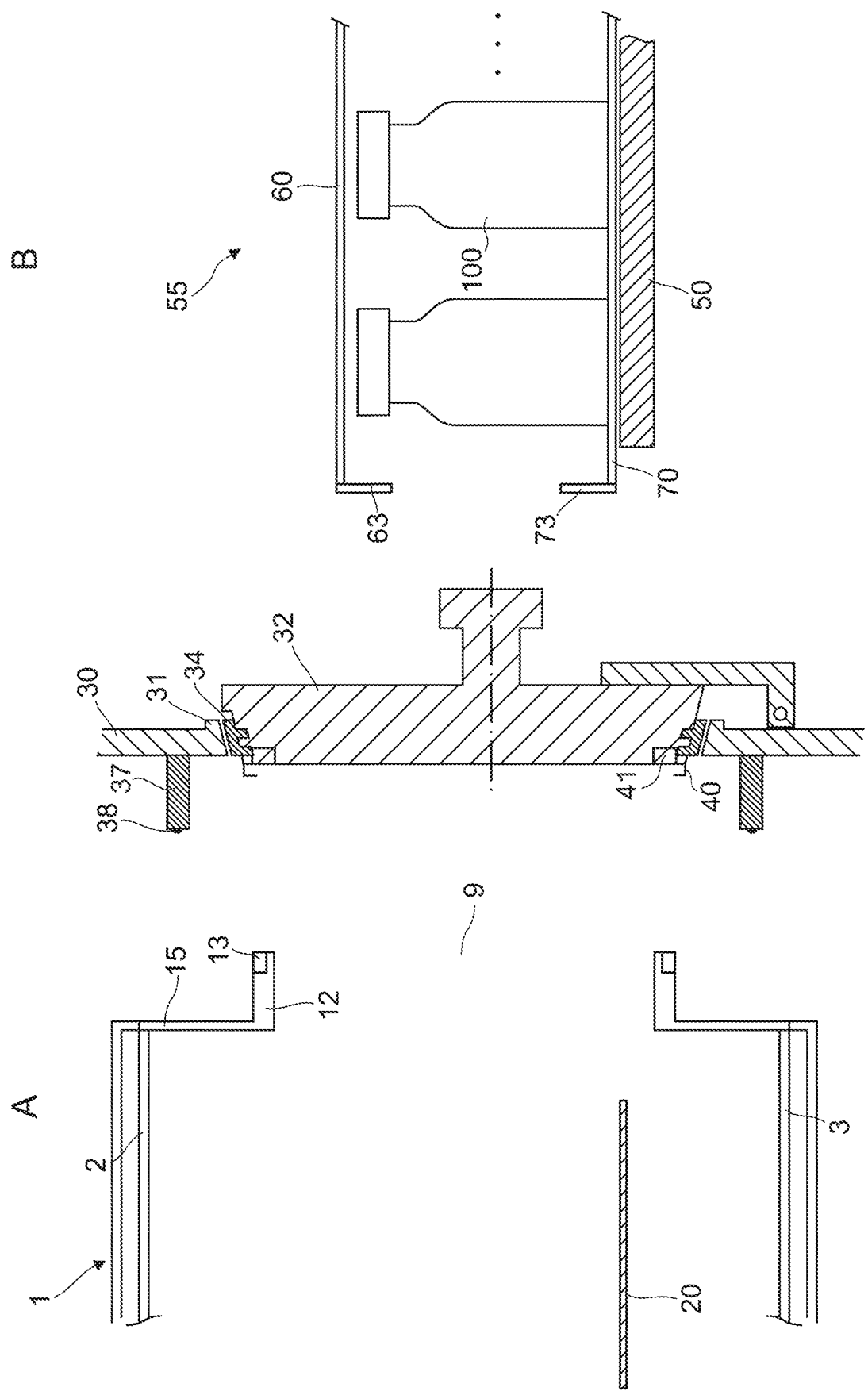

Once the supporting structure 55 has been pushed onto the guide rail 50 in the clean room B, as shown in FIG. 3*e*, the transfer port door 32 is then closed again. Then, the containers 100 can be removed from the supporting structure 55 in the clean room B, as described in more detail below, and are then ready for a further processing in the clean room B, e.g. for filling the containers 100 under standard or high purity clean room conditions.

Because the outside of the protective sheet 10 has been brought in abutment to the outside of the transfer port door 32 before opening the transfer port door 32, in the opened position of the transfer port door 32 shown in FIG. 3*d* germs or contaminations cannot enter the inside space of the clean room B, neither from the outside of the protective sheet 10 or cover nor from the outside of the transfer port door 32, and neither contaminate the containers 100 when these are transferred into the clean room B. This effect is further promoted if a circumferential seal is provided on the outside of the transfer port door 32, as this is the case in the embodiment of FIGS. 2*a* to 2*d* (reference numeral 39), and if the protective sheet 10 or cover is brought in abutment with the transfer port door 32 before opening it, for sealing the gap 29 (see FIG. 2b) between the outside of the protective sheet 10 or cover and the outside of the transfer port door 32.

As shown in FIG. 3e, the transport container 1 is finally removed from the side wall 30 of the clean room B and moved back into the space A after closing the transfer port door 32. After releasing the transport container 1 in the space A, the access opening 9 may remain open, as shown in FIG. 3e, or alternatively it may be closed again, for example, it may be closed temporarily by means of a cover (not shown), so that additional impurities cannot enter the inside space of the transport container 1.

As will become apparent to the person skilled in the art, the containers 100 can be transferred in a corresponding manner from the clean room B back into the same or a different transport container 1 by reversing the sequence of the steps shown of FIGS. 3e to 3a, which will be explained below in more detail with reference to FIG. 7c.

The afore-mentioned temporary locking of the transport container 1 at the side wall 30 of the clean room B can be implemented in various ways. For example, adjustable locking means, for example, pivotally mounted arms having hook-shaped front ends, may be provided at the side wall 30 of the clean room B, which allow an unimpeded approach of the transport container in a starting position and can then be transferred into a locking position, for example, by pivoting toward the transport container, to be in engagement with recesses or depressions disposed there. In the locking position, the transport container 1 is temporarily locked at the side wall 30 of the clean room B. The locking may also be performed by means of a bayonet mechanism or the like, for example by providing a rotating ring on the side wall 30 of clean room B, which engages in corresponding structures on the front side wall 15 of the transport container 1 upon rotation, or by displacement of the transport container 1 laterally when approaching the side wall 30, which results in a positive-fit engagement of locking elements, for example of inclined surfaces, on the front side wall 15 of the transport container 1 and on the side wall 30 of the clean room B.

FIG. 8c illustrates a further procedure for the temporary fixation of the transport container 1 at the side wall 30 of a clean room B. According to FIG. 8c, clamping strips 309, which are L-shaped in profile, are provided on the outside of the side wall 30 along the bottom edge of the transfer port door 32, which can be pivoted away from the side wall 30 and pivoted towards the latter again. In the closed position according to FIG. 8c, in which the clamping strips 309 are pivoted toward the side wall 30, the clamping strips 309 grip behind the flange 11 projecting beyond the bottom edge of the transport container 1 and thus the transport container 1 is pulled toward the side wall 30. A circumferential resilient seal may be provided around the access opening of the transport container or around the transfer port door 32, as described above. For releasing the transport container 1 from the side wall 30, the clamping strips 309 may be pivoted away from the side wall 30 in order to release the flange 11.

Of course, the clamping strips 309 may be provided in a corresponding manner on the side wall 30 so that they can be displaced either horizontally or vertically to clamp the flange 11 of the transport container 1 temporarily.

Alternatively, the front side wall 15 of the transport container could also be pulled or pushed temporarily against the side wall 30 of the clean room B by means of a suction device, or electrically, magnetically or pneumatically.

Figure 4A:
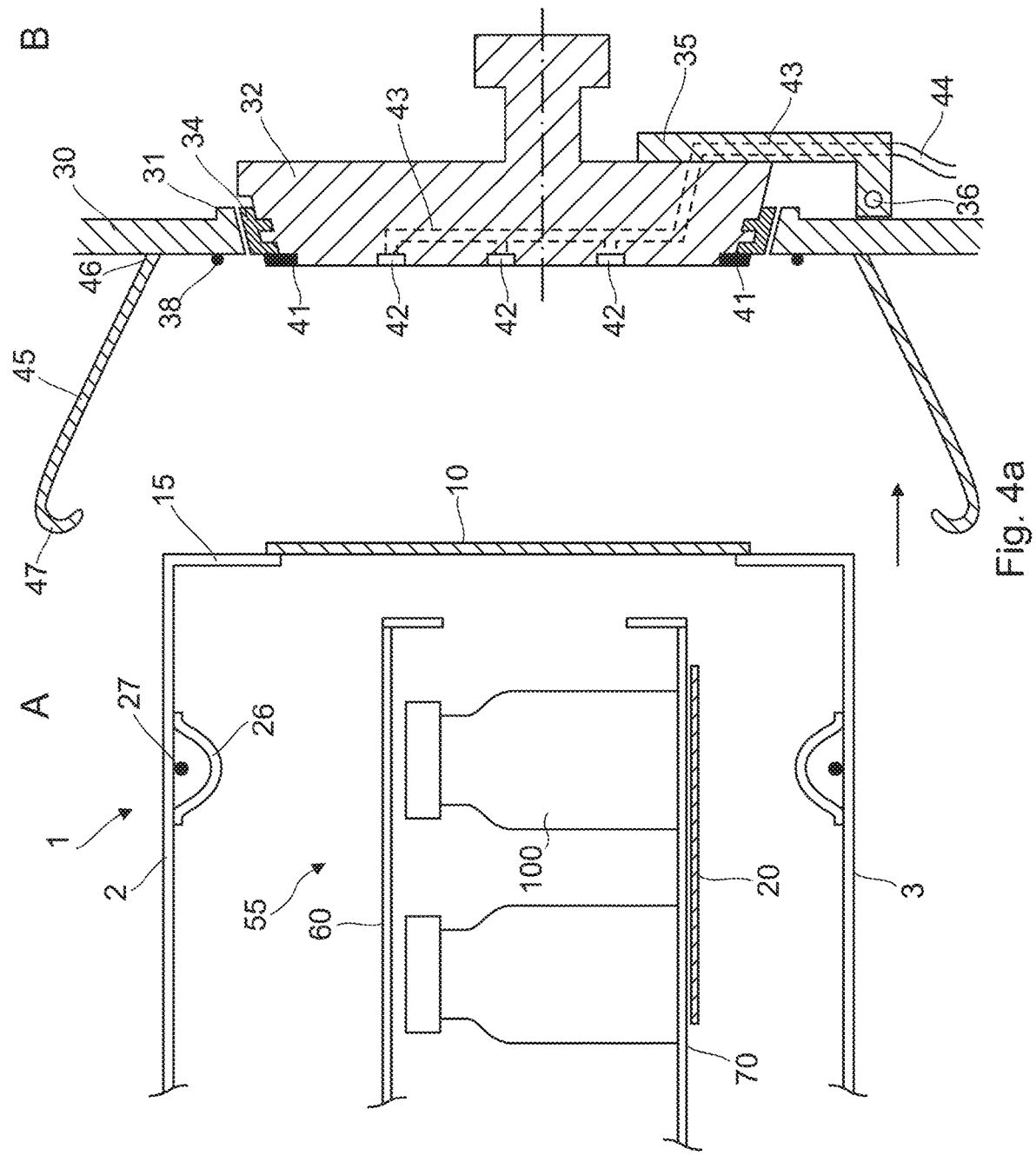
Figure 4B:
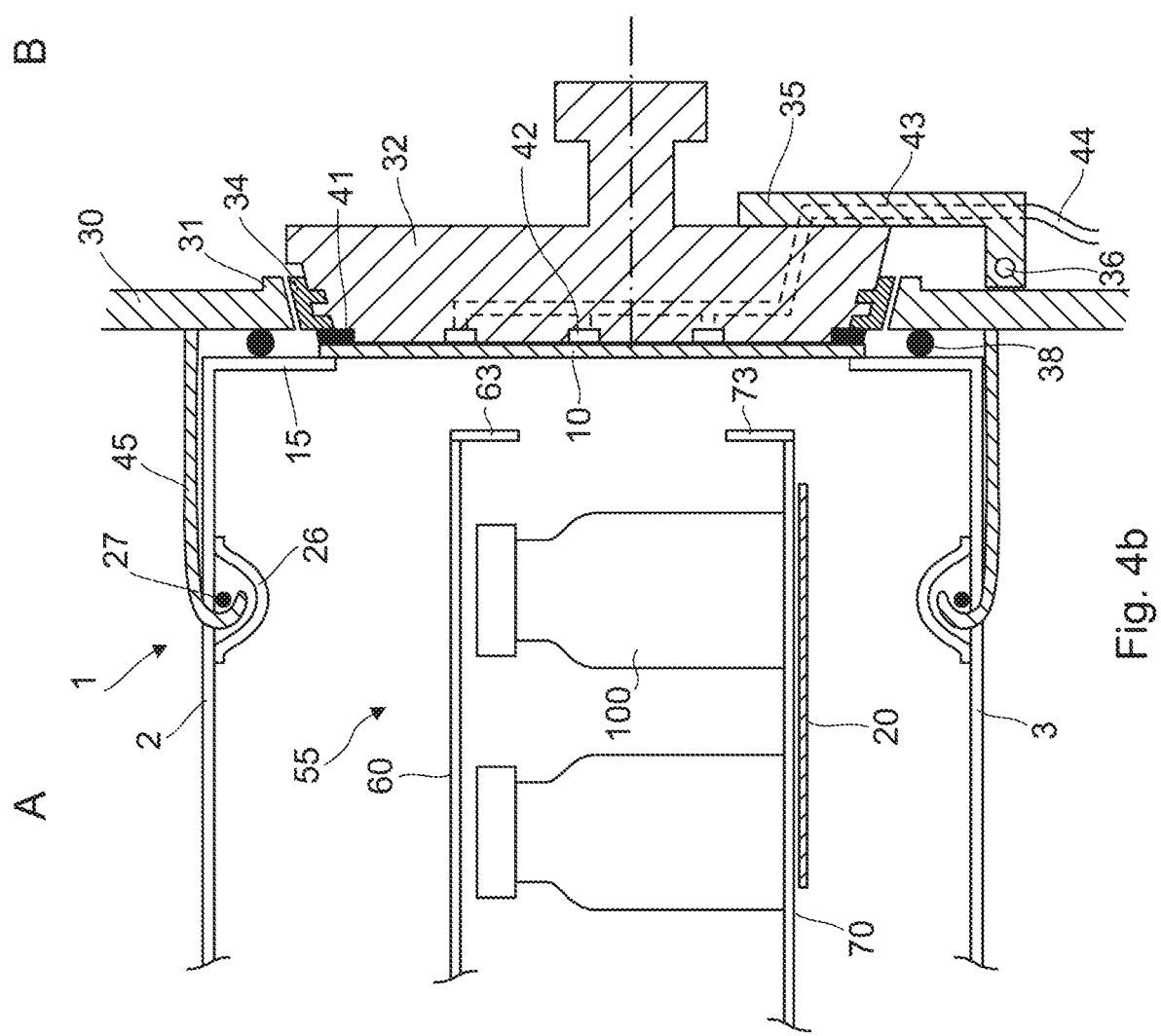

Referring to FIGS. 4a to 4c, a further variant for the temporary fixation of the protective sheet 10 or cover at the outside of the transfer port door 32 will be described in the following. This embodiment relies on a transport container 1 according to FIG. 1a having a flat front side wall 15 on which an access opening is formed and on which the protective sheet 10 or a cover is bonded. According to FIG. 4 a plurality of suction heads 42 are provided on the outside of the transfer port door 32 corresponding to the protective sheet 10 or cover, which are connected with a connecting line to a suction device (not shown) via a suction line 43, which extends in the transfer port door 32 and in the pivot arm 35, which is used to apply a negative pressure to the suction heads 42. Starting from the position shown in FIG. 4a, the transport container 1 is brought in proximity to the transfer port door 32 until the position as shown in FIG. 4b is reached, in which the front side wall 15 of the transport container 1 directly abuts the seal 38 and in which the protective sheet 10 or cover rests directly on the outside of the transfer port door 32. By activating the suction device (not shown), the protective sheet 10 or cover is pulled by the suction heads 42 against the outside of the transfer port door 32. In this position, the adhesive rim on the front side wall 15 of the transport container 1 is heated by activating the heating device 41 until the adhesive is sufficiently softened, so that the force exerted by the suction heads 42 becomes larger than the adhesive strength of the adhesive and the protective sheet 10 or cover are pulled from the front side wall 15 of the transport container 1 when the transfer port door is opened, as shown in FIG. 4c.

If the protective sheet 10 is a gas-permeable protective sheet, for example, a gas-permeable Tyvek® protective sheet, gas-impermeable regions may be provided on the gas-permeable protective sheet at positions corresponding to the positions of the suction heads 42, for example, they may be formed by forming circular gas-impermeable portions, in particular by applying a gas-impermeable coating material or a gas-impermeable coating at these positions, so that the protective sheet 10 or cover is then pulled against the outside of the transfer port door 32 by means of the suction heads 42 and by applying a vacuum.

As compared to the afore-mentioned embodiment, according to FIGS. 4a to 4c the temporary fixation of the transport container 1 is accomplished by means of a trough-shaped recess 26 formed on the outside of the transport container 1 in which a holding web 27 is provided. By adjusting pivotally mounted locking arms 45, starting from the opened position of FIG. 4a, to the locking position of FIG. 4b, the hook-shaped front ends 47 of the latching arms engage behind the holding webs 27 on the outside of the transport container 1 for temporary fixation of the transport container 1. Here, also the length of the latching arms 45 may be adjustable in order to firmly pull the transport container 1 against the side wall 30. Subsequently, the cover 10 is coupled with the outside of the transfer port door 32. This may also be performed by activating the suction heads 42 and the heating device 41. Thus, first an adhesive, which is used for bonding the cover 10 onto the front side wall 15 of the transport container 1, is softened. When the pulling force exerted by the suction heads 42 exceeds the adhesive strength of the adhesive 10, the cover 10 is sucked against the outside of the transfer port door 42.

Of course, the coupling and the removal of the cover 10 may also be performed in other ways. Expressly, for example, a mechanical coupling of the outside of the cover 10 with adjustable grippers, with form-fitting structures on the outside of the transfer port door 32, such as latching knobs and associated, opposite recesses or the like is contemplated. Generally, a temporary electrical, magnetic or pneumatic coupling of the outside of the cover 10 with the outside of the transfer port door 32 is further contemplated.

Subsequently, the transfer port door 32 is opened, as shown in FIG. 4*c*, whereby the cover 10 is removed from the front side wall 15 of the transport container 1. Subsequently, the transfer of the supporting structure 55 together with the containers 100 accommodated therein via the access opening 9 of the transport container 1 into the inside space of clean room B is carried out. Because the outside of the cover 10 has been brought into abutment to the outside of the transfer port door 32 before opening the transfer port door 32, in the opened position according to the FIG. 4*c* germs or contaminants cannot enter the inside space of the clean room B, neither from the outside of the cover 10 nor from the outside of the transfer port door 32, or contaminate the containers 100 while these are transferred into the clean room B. This effect is further promoted, if a circumferential seal is provided on the outside of the transfer port door 32, as this is the case in the embodiment of FIGS. 2*a* to 2*d* (reference numeral 39), and if the cover 10 is brought in abutment with it before opening the transfer port door 32, for sealing the gap 29 (see FIG. 2*b*) between the outside of the cover 10 and the outside of the transfer port door 32.

After closing the transfer port door 32, the containers 100 may then be further processed in the clean room B. Subsequently, the latching elements 47 are disengaged from the corresponding counter-elements (depressions) 25 by pivoting back the latching arms 45 into their initial position. Afterwards, the transport container 1 is removed from the side wall 30 of the clean room B, as set forth above.

The containers 100 may be accommodated in the transport container 1 in a supporting structure 55, as described hereinafter with reference to FIGS. 5*a* to 5*e*, which are intended to enable an easier handling of the plurality of containers 100 and which shall also serve as an additional protection of the containers 100 against an accidental intrusion of impurities and germs.

Figure 5C:
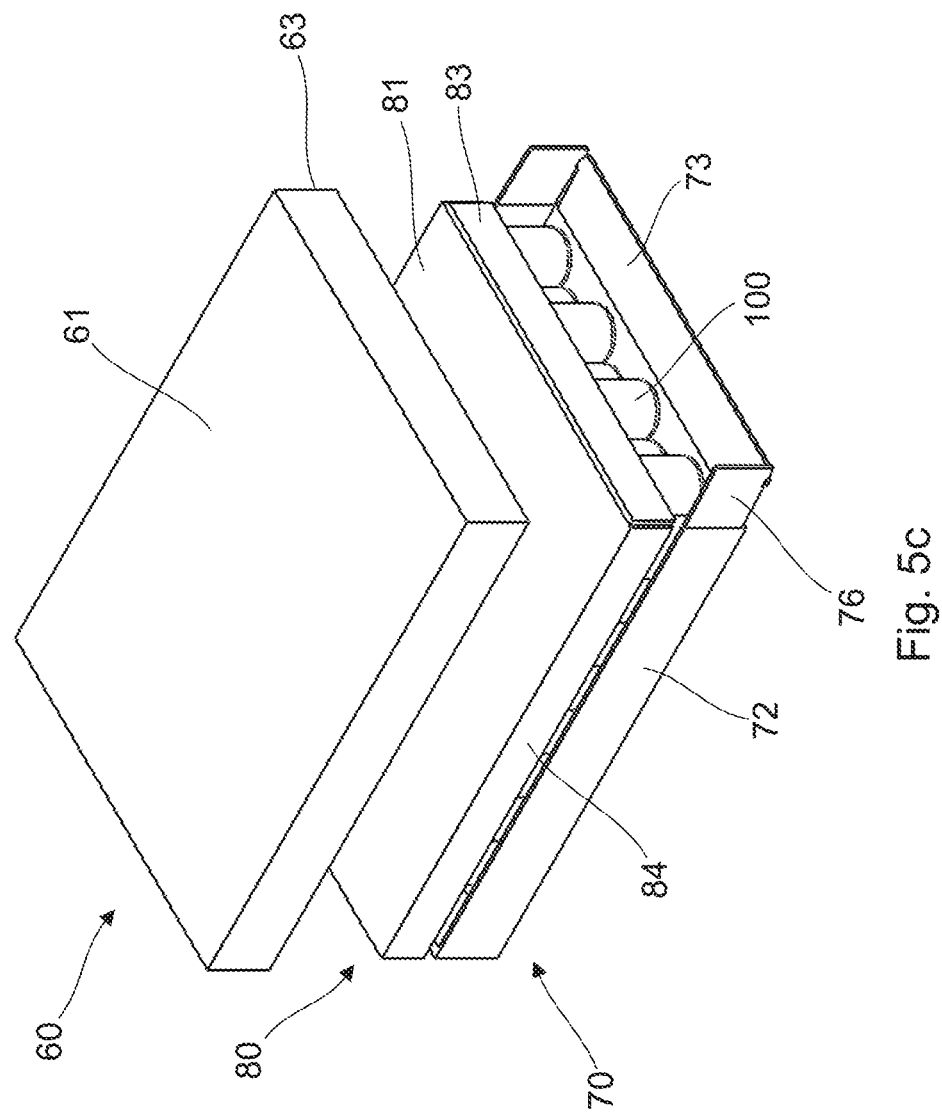

According to FIGS. 5*a* and 5*b*, the supporting structure 55 comprises a box-shaped upper part 60 and a box-shaped bottom part 70. The upper part 60 has a flat rectangular bottom 61, two side walls 62, and a front and rear side wall 63 that each protrude vertically from the bottom 61. The bottom part 70 has a corresponding shape and comprises a flat rectangular bottom 71 and two side walls 72, each of which projecting perpendicularly from the bottom 71. According to FIG. 5*c*, the front and rear side walls 73 of the upper part 70 can be folded down and then forms a common plane (flat surface) together with the bottom 71, and is folded-up again for forming the box-shaped bottom part 70 at a suitable time.

When the front side wall 73 is folded down in the position shown in FIG. 5*c*, the containers 100 can be pushed easily into the bottom part 70 from a supporting surface (not shown) which is preferably flush with the upper surface of the bottom 71 and with the front side wall 73 that is folded down. After pushing the containers 100 into the bottom part 70, the side flaps 76, which are formed at the front ends of the side walls 7, and the front side wall 73 are folded back and coupled with each other to form a front side wall, which also projects perpendicularly to the bottom 71 of the bottom part 70. The height of the side walls 72, 73 is less than the height of the containers 100.

Preferably the containers 100 are accommodated in the supporting structure 1 free of play. The containers 100 may be accommodated in the bottom part 70 with direct wall-to-wall contact, to accomplish the greatest possible packing density. According to further embodiments, elastic or inelastic inserts may be provided between all containers 100, for example as partition walls, for preventing a contact of directly adjacent containers in the bottom part 70. According to further embodiments, such partition walls may also be provided as elastic or inelastic separation strips, for separating rows of containers from each other and preventing a movement of rows of containers.

In the embodiment of FIG. 5*b* the box-shaped upper part 60 may be placed directly on the upper ends of the containers 100 for preventing intrusion of impurities from above into the containers that are not yet sealed. As shown in FIG. 5*b*, however, also an additional intermediate layer, for example, a thin plastic plate or plastic film, or a box-shaped intermediate part 80 shown in FIG. 5*b* may be placed on the upper ends of the containers before the upper part 60 is put on, for preventing the intrusion of particles into the still open ends of the containers 100 even when the upper part 60 is removed, as shown in FIG. 5*c*. Here, the side walls 83, 84 prevent an inadvertent lateral sliding of the intermediate part 80 from the containers 100.

Figure 5D:
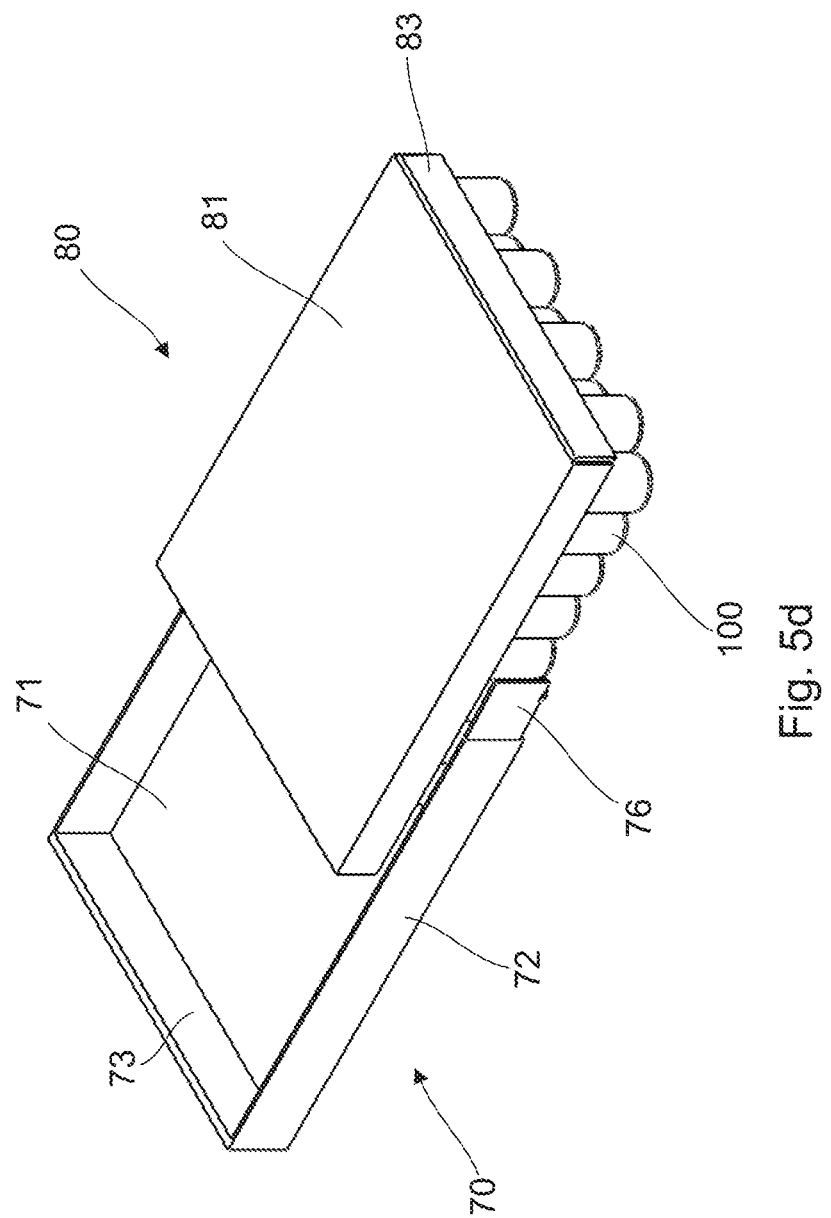

After removal of the box-shaped upper part 60 and folding down the front side wall 73 of the bottom part 70 as shown in FIG. 5*d*, the containers 100 may be pushed out of the bottom part 70 by displacement of the intermediate part 80. Finally, by lifting and removing the intermediate part 80, an access to the containers 100 becomes possible, for the treatment or further processing, as shown in FIG. 5*c*. These steps for opening the supporting structure are performed in the clean room B having the lower particle concentration.

After the treatment or processing of the containers 100 in the clean room B and optionally after sealing of the containers 100, the above steps may be carried out in the reverse sequence in order to form again the supporting structure 55 shown in FIG. 5*a*. During the treatment or further processing of the containers 100 in the clean room B, the components of this supporting structure 55 are not further contaminated due to the lower particle concentration prevailing in the clean room B, so that the supporting structure 55 together with the containers 100 accommodated therein continues satisfying the highest demands with regard to sterility after their treatment or processing.

The bottom 71, in particular the bottom 71 of the bottom part 70, may be coated with a sliding layer for facilitating the insertion of the containers 100 described above. The sliding layer may consist of a polymer and an adhesion promoter. Preferably, the sliding layer consists at least partially of a mixture of an aromatic silane and an aliphatic silane. Other suitable materials for the bottom part 70 are, for example, polyamide or polyoxymethylene (POM).

For a further transport the supporting structure 55 shown in FIG. 5*a* may be sterile sealed in a tube or packaging bag made of plastic, as shown in FIG. 1*h*, which can take place directly in the clean room B. In principle, the supporting structure 55 may, however, be transferred back into the upstream clean room A, in particular into a transport container located there, by performing the steps described above with reference to FIGS. 2 to 4 in reverse sequence, which will be described in more detail below with reference to FIG. 7*c*.

For the temporary storage of the containers in a predetermined geometric arrangement, in particular in a two-dimensional matrix arrangement, any other supporting structure may be used, such as described with reference to FIGS. 6*a*-6*c* by way of example. Such supporting structures may cover the upper ends of the containers accommodated therein, as described above, which, however, is not absolutely necessary.

Thus, FIG. 6a shows an example of a supporting structure formed in two pieces, comprising a flat bottom part 70 and a box-shaped upper part 60. On the flat bottom part 70 a plurality of square-shaped receptacles 77 is formed by the circumferential side wall 74 and by the plurality of transverse webs 75 extending in parallel with each other and intersecting each other perpendicularly, containers 100 being accommodated in these square receptacles 77. Also in the box-shaped upper part 60 a plurality of square-shaped receptacles 67 is formed by the circumferential side wall 65 and by the plurality of transverse webs 66 extending in parallel with each other and intersecting each other perpendicularly. The transverse webs 66 of the upper part 60 are arranged corresponding to the transverse webs 75 of the bottom part 70, so that the containers 100 placed on the bottom part 70 are accommodated in receptacles which are formed by the transverse webs 66 of the upper part 60 and by the transverse webs 75 of the bottom part 70 when placing the upper part 60 onto the bottom part 70, whereby a collision of directly adjacent containers 100 in the regular array of containers 100 thus-formed can be prevented.

Figure 6B:
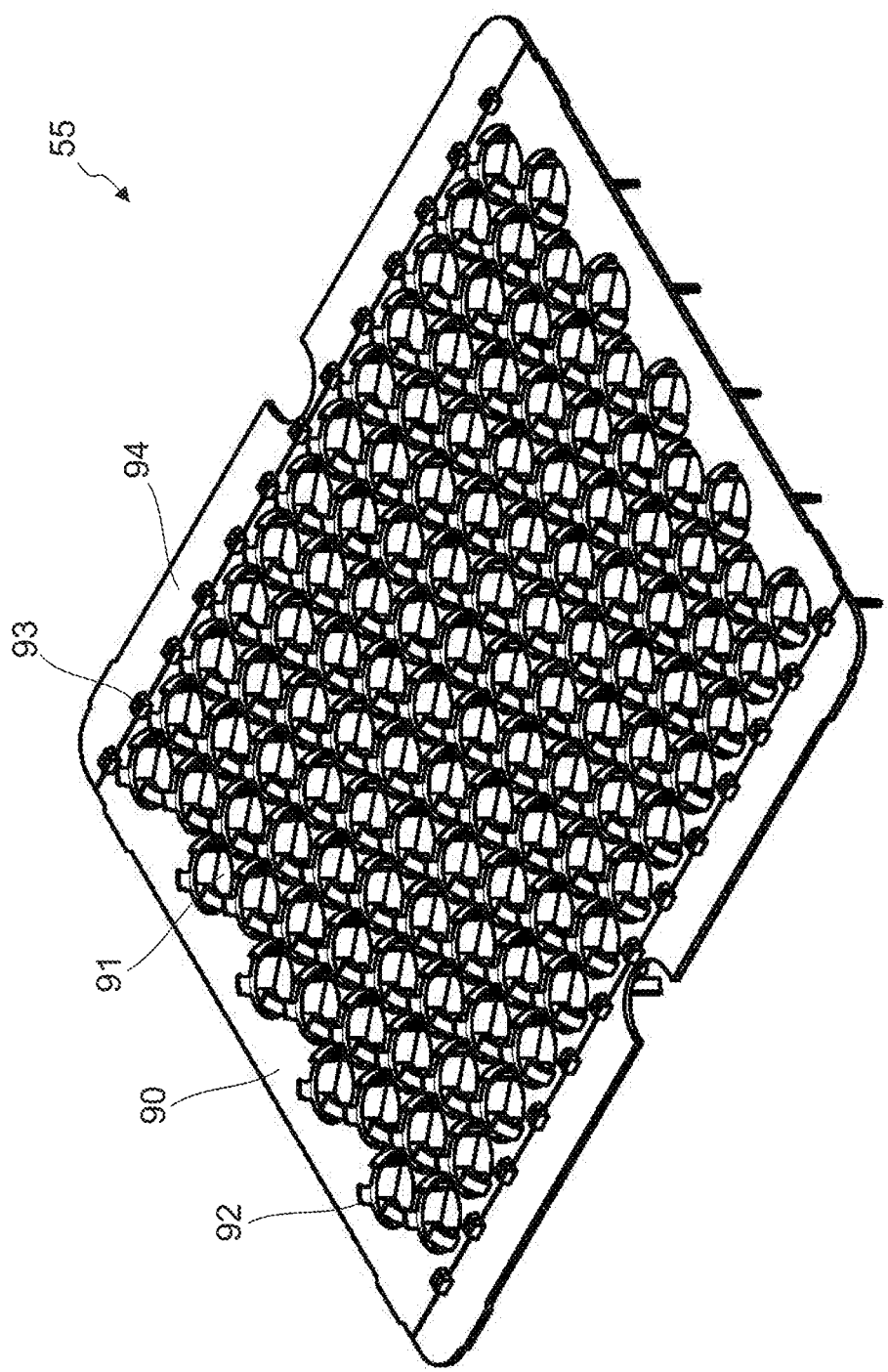

FIG. 6b shows another example of a supporting structure 55 for supporting a plurality of containers, which is formed in one piece, comprising a flat rectangular carrier 90 that is formed of a plastic, for example, by punching out or injection molding, and a plurality of openings 91 for accommodating the containers (not shown). The openings 91 are arranged in a regular two-dimensional matrix array of rows and columns extending perpendicularly that are arranged at equidistant intervals to each other and displaced relative to each other in a repeating array configuration. Resilient holding tongues 92 protrude arcuately from the upper side of the carrier 90, projecting into the associated openings 91, if viewed in a plan view. The resilient holding tongues 92 are preferably formed integrally with the flat carrier 90, for example, by a one component (1K) plastic injection molding process or a two component (2K) plastic injection molding process. The containers may rest loosely on the resilient holding tongues 92 at least with play in radial direction and preferably with play both in radial and axial direction, for compensating tolerances. The edges 94 of the planar carrier 90 can be pivoted away, for further reducing the base area of the carrier 90, for example, when the carrier 90 together with the containers shall be transferred into a further processing station with limited space, for example, into a freeze dryer. For this purpose, the edges 94 are connected with the respective carrier 90 by means of hinges 93, which are, for example, formed of a plastic material in the form of film hinges or snap-action hinges or spring hinges and which are formed integrally with the carrier 90.

Figure 6C:
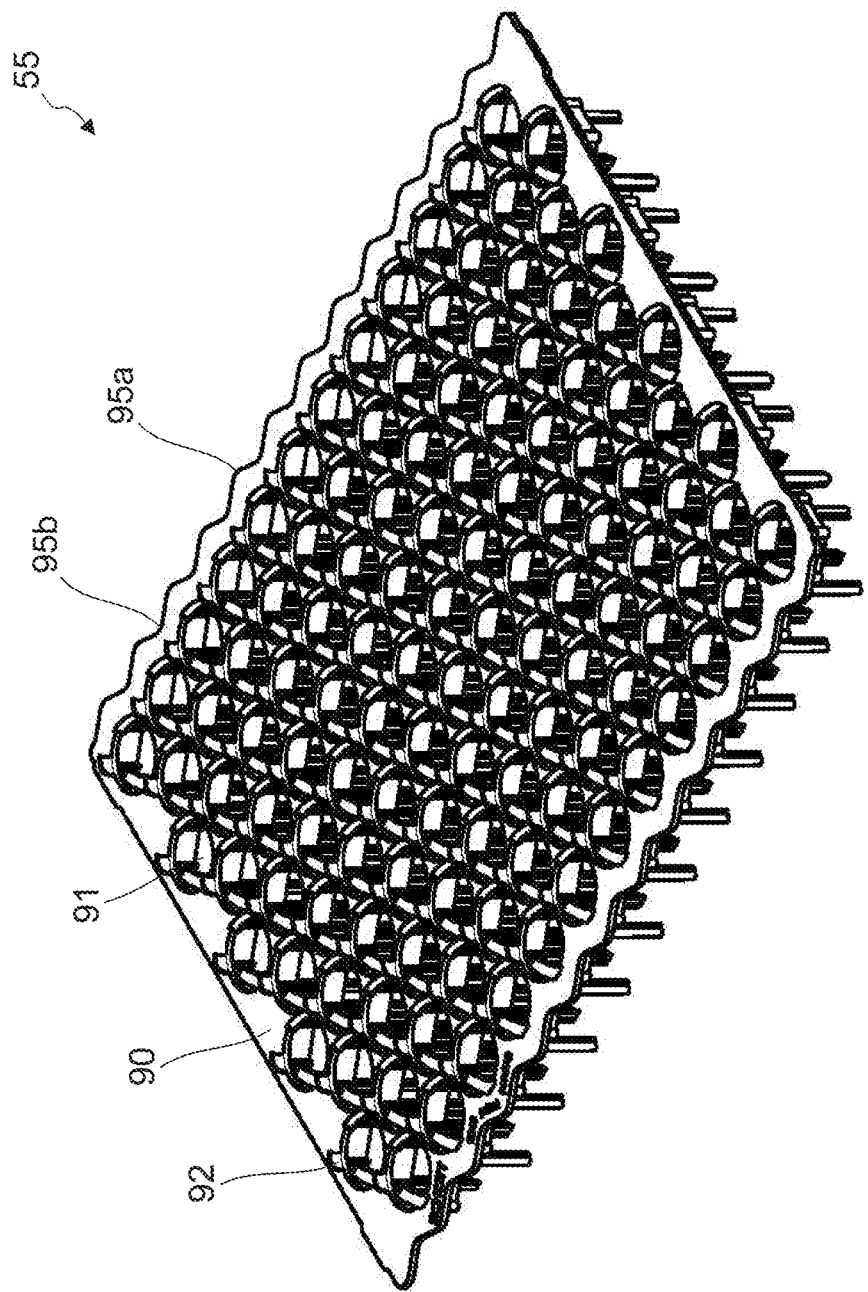

FIG. 6c shows a further variant to the supporting structure shown in FIG. 6b, wherein a plurality of projections 95b and recesses 95a are formed at the edge of the flat carrier 90 that can be engaged temporarily and in a form-fitting manner with corresponding projections and recesses of an adjacent carrier (not shown) that is of identical configuration, for coupling the two carrier together temporarily and displacing them together.

In the following, a process for transferring a plurality of containers from a transport and packaging container into a clean room in accordance with a first embodiment of the present invention will be described with reference to the flow diagram of FIG. 7a. Here, it is assumed that the containers are provided in a transport and packaging container, which is sterile sealed in a packaging unit, for example, sealed in a plastic bag. The containers may be vials, ampoules, cartridges or syringes or injection containers or any other container of a glass or plastic material. Conveniently, the packaging of the containers in the transport and packaging container and in the packaging unit takes place on the part of the manufacturer. The packaging unit is then supplied to a further processing facility, for example to a facility for filling pharmaceuticals. Here, the transport and packaging container described above may be sealed sterile and packaged in a plastic tube, as shown in FIG. 1h.

This packaging unit is first introduced into a first space, which may be a clean room with a relatively high particle concentration (step S1).

For the transfer into a clean room with a lower concentration of particles the transport and packaging containers together with the plurality of containers accommodated therein is first removed from the packaging unit (step S2) and the transport and packaging container is positioned near the side wall of the clean room in such a manner that a side wall of the transport and packaging container is positioned near the transfer port door of the clean room (step S3). This may be effected in the upstream clean room at a higher particle concentration than in the clean room in which the containers are to be further processed later, which has a lower particle concentration for this purpose. In principle it may be sufficient for such a sterile transfer of the containers, if the gap between the side wall of the transport and packing container and the transfer port door or the side wall of the clean room with the lower concentration of particles is relatively narrow, so that the probability for the intrusion of impurities into this gap and thus into the clean room with the lower particle concentration is low. Preferably, however, the side wall of the transport and packaging container is positioned so close to the side wall of the clean room with the lower concentration of particles that the aforesaid gap is sealed by sealing means, as described above, and that the intrusion of impurities into this gap is prevented.

Subsequently, the side wall of the transport and packaging container and the transfer port door are opened simultaneously, so that an access opening of the transport and packaging container is in communication with an inside space of the clean room with the lower concentration of particles and the plurality of containers can be transferred from the transport and packaging container into the inside space of the clean room (step S4). Preferably, to that end the cover or protective sheet provided on the side wall of the transport and packaging container is coupled temporarily with the transfer port door, so that the transfer port door can be opened together with the cover or protective sheet temporarily fixed to it, as described above.

Then, the transfer port door is closed, so that the containers can then be further processed in the clean room with the lower particle concentration. Afterwards, the transport and packaging container is removed again from the side wall of the clean room, for releasing the transfer port door again for the transfer of another plurality of containers from another transport and packaging container into the clean room.

Figure 7B:
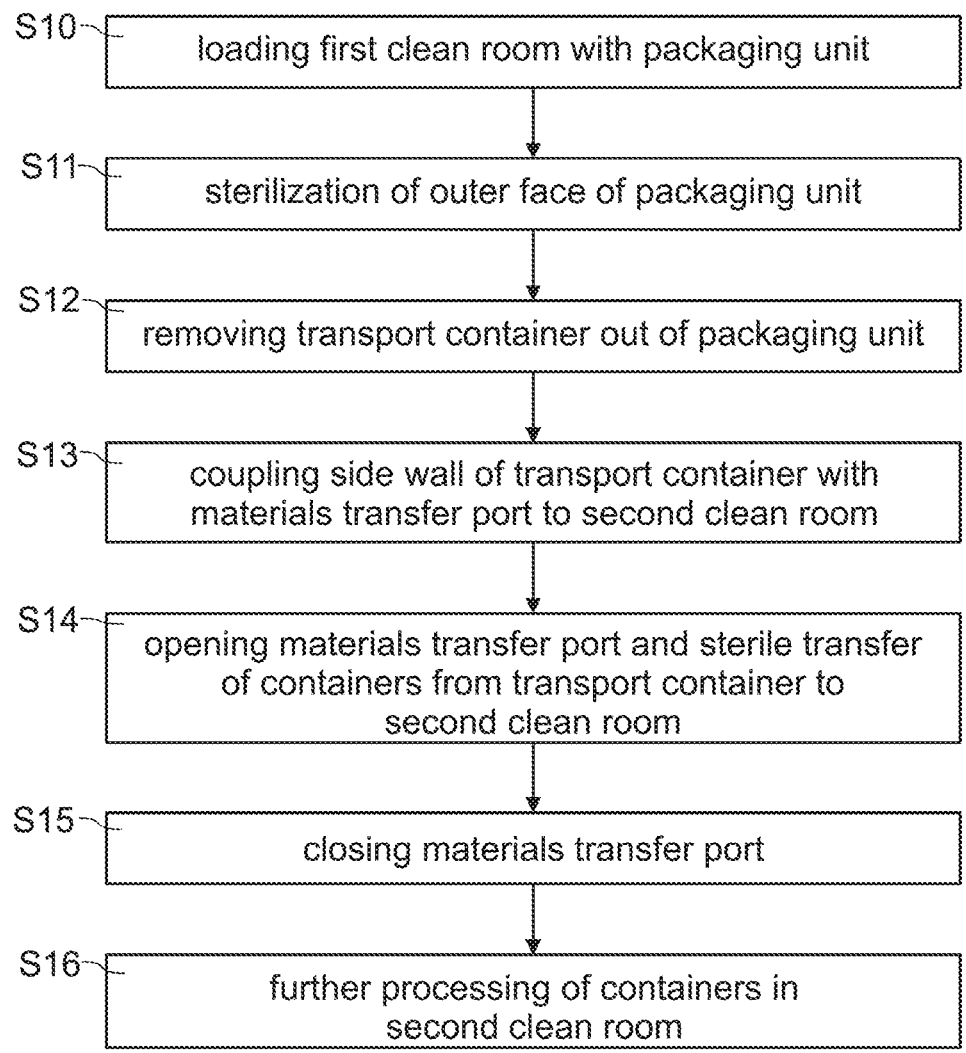
FIG. 7b shows a method for transferring a plurality of containers for the storage of substances for medical, pharmaceutical or cosmetic purposes into a clean room according to a further embodiment of the present invention.
Figure 7C:
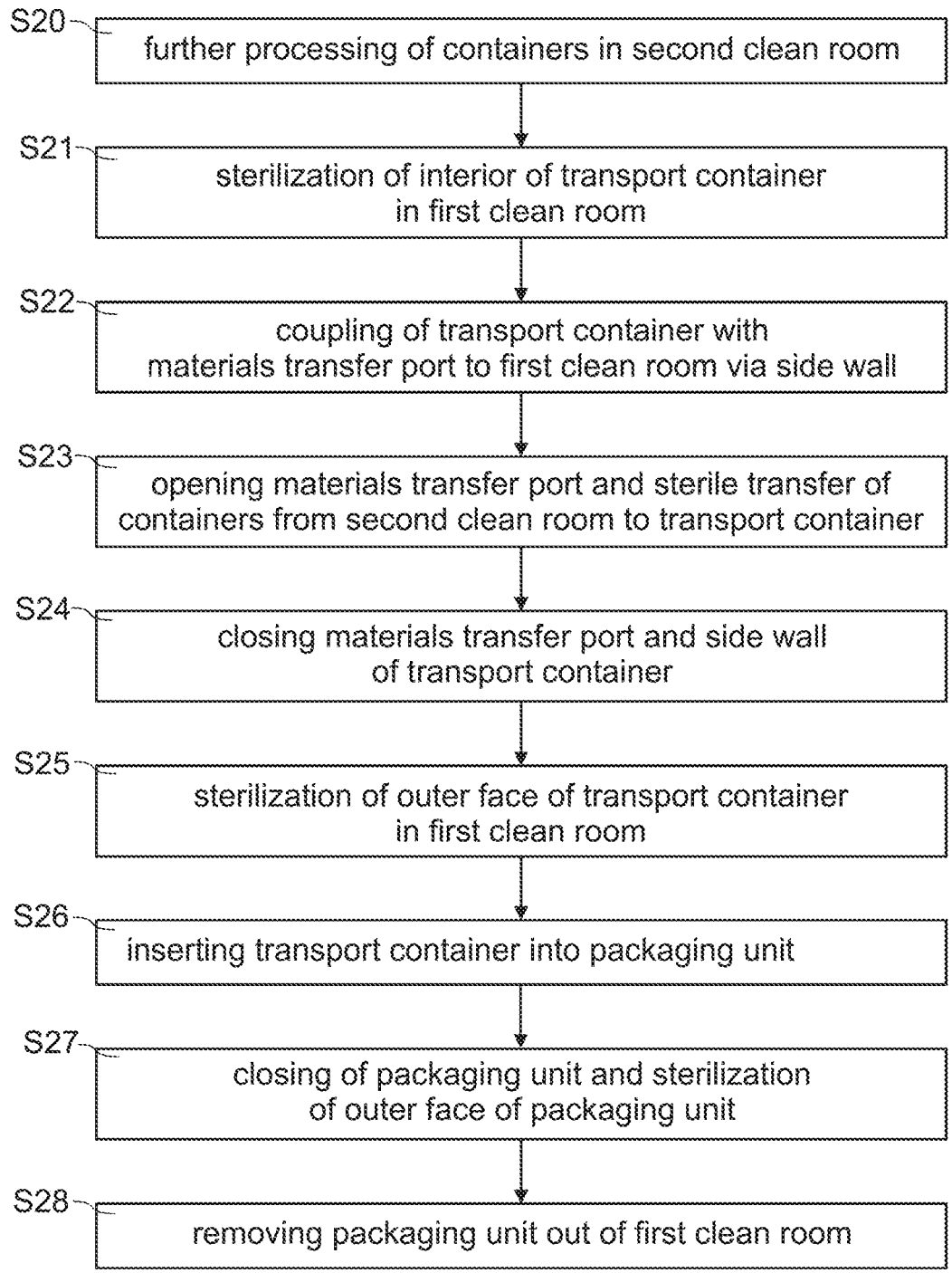
FIG. 7c shows a method for transferring a plurality of containers for storage of substances for medical, pharmaceutical or cosmetic purposes from a clean room into a transport and packaging container to form a packaging structure according to the present invention.

The flowchart of FIG. 7b summarizes the steps of a method of a second embodiment of the present invention. Here, it is assumed that the containers are provided packaged in a packaging unit, for example, sealed in a sterile packaging bag of a plastic material, in which at least one transport and packaging container is stored, as set forth above. The outside of this packaging unit is introduced into a first space, in particular into a first clean room with a higher concentration of particles (step S10). Then, the outside of the packaging unit is sterilized (step S11), for example by vapor sterilization using a gas (for example by means of an ethylene oxide (EO) sterilization process) or by irradiation. Then the packaging unit is opened and the at least one transport and packaging container is removed from the packaging unit (step S12). The transfer of the containers into the clean room is carried out in steps S13 and S14 in a similar manner as described above with reference to FIG. 7a. FIG. 7b is based on the assumption that the side wall of the transport container or the cover or protective sheet provided on this side wall is first coupled to the outside of the transfer port door (step S13) before the transfer port door is opened. For sterile removal and transfer of the containers it may be sufficient, however, if the side wall of the transport and packaging container is properly coupled to the transfer port door of the clean room, which may be accomplished, for example, also by sealing the gap between the cover or protective sheet and the transfer port door by means of a seal provided around the cover or protective sheet, of which examples are shown in FIGS. 1a to 1c, but which may also be provided on the side wall of the clean room.

A sterile removal and transfer of the containers can be performed more reliably by temporarily coupling the cover or protective sheet on the side wall of the transport and packaging container with the transfer port door, as outlined above.

Then, the side wall of the transport and packaging container and the transfer port door are opened and the plurality of containers is transferred from the transport and packaging container into the inside space of the clean room with the lower particle concentration (step S14). After closing the transfer port door (step S15), the containers may then be further processed in this clean room (step S16), as set forth above.

Finally, the transport and packaging container is removed again from the side wall of the clean room, for releasing the transfer port door for the transfer of another plurality of containers from another transport and packaging container into the clean room.

Between the step S13 (coupling the transport container . . . ) and S14 (opening the transfer port door . . . ) optionally a further step may be provided for sterilizing particularly the front side wall of the transport container with the cover or protective sheet provided thereon. Suitable processes for this purpose are in particular: purging the front side wall with a flow of ethylene oxide (ETO), irradiating the front side wall with gamma radiation or electron beams, purging the front side wall with vapor (under controlled conditions), or newer methods, such as oxidative low temperature sterilization. For this purpose, corresponding sterilization devices may be provided in the region of the transfer port door on the outside of the clean room with the lower concentration of particles, in particular gas outlets or irradiation devices. The sterilization is carried out preferably after sealing the gap between the front side wall of the transport container and the side wall of the clean room against the environment. Generally, however, the sterilization may also be carried out without sealing that gap, in particular if the transport container has been positioned in such close proximity to the side wall that the width of the gap is already relatively small in comparison with the dimensions of the transport container.

The sequence of steps described above can be carried out essentially in reverse sequence, for transferring the containers from the clean room with the lower concentration of particles back into a transport and packaging container after their further processing in the clean room, wherein the transport and packaging container is then again packaged sterile in a packaging unit, if necessary. This will be described below by way of example with reference to FIG. 7c.

After the further processing of the containers in the clean room with the lower particle concentration (step S20), first the inside space of transport and packaging container may be sterilized in the upstream clean room with the higher concentration of particles prior to the transfer of the containers into the transport and packaging container (step S21). However, this step is not absolutely necessary, or can be carried out only after the transfer of the containers into the transport and packaging container, for example, by means of a flow of gas using an ethylene oxide (ETO) sterilization process (in particular, if a gas-permeable protective sheet is provided at the transport and packaging container).

Afterwards, the coupling of an openable side wall of the transport and packaging container with the transfer port to the clean room with the lower concentration of particles is performed in step S22 in the same manner as described above. Then, the transfer port is opened and the containers are transferred from the clean room with the lower concentration of particles into the transport and packaging container (step S23). For this purpose, it is preferred that the side wall of the transport container or the cover or protective sheet provided thereon is first coupled to the outside of the transfer port door before opening the transfer port, as described above. After transferring the containers into the transport and packaging container the transfer port door is closed again (step S24) and the access opening on the side wall of the transport and packaging container is sterile sealed again by a cover or protective sheet. To this end, the cover or protective sheet coupled with the transfer port door may be released after closing the transfer port door and the cover or protective sheet may be properly attached to the side wall of the transport and packaging container to close the access opening again.

If the cover is, for example, a gas-permeable or gas-impermeable closure lid it may be sufficient for this purpose to press the closure lid onto the side wall of the transport and packaging container or any other suitable mechanical coupling of the closure lid with the side wall of the transport and packaging container may be sufficient, e.g. by screwing on the closure lid. For this purpose, suitable adjusting or handling devices may be provided on the outside of the transfer port door or of the side wall of the clean room with the lower particle concentration, for example mechanical gripping devices, as set forth above. Of course, such a closure lid may also be bonded properly on the side wall of the transport and packaging container.

On the other hand, is the lid is, for example, a gas-permeable protective sheet, the protective sheet may be properly bonded on the side wall of the transport and packaging container. For this purpose, it may be sufficient to actuate the heaters 41, which have been described above with reference to FIGS. 3a to 3e and FIGS. 4a to 4c, again for softening again the adhesive rim on the side wall of the transport and packaging container, which is formed circumferentially around the access opening, and then to press the protective sheet properly onto the side wall and allow the adhesive rim to cool again. For this purpose, suitable adjusting devices may be provided on the outside of the transfer port door, for example a circumferential plunger formed corresponding to the adhesive rim, for pressing the protective sheet onto the side wall of the transport and packaging container in the region of the adhesive rim.

Then, the outside of the transport and packaging container is sterilized in the upstream clean room with the higher concentration of particles in step S25, which is conveniently carried out after removing the transport and packaging container from the side wall of the clean room with the lower particle concentration.

Afterwards, a further sterilization of the inside space of the transport and packaging container may be carried out, for example for sterilizing the outer surfaces of the containers accommodated therein. This may be performed in particular by a flow of gas using an ethylene oxide (ETO) sterilization process, if a gas-permeable protective sheet is provided on the transport and packaging container as a cover covering the access opening.

The further transport of the containers may be performed directly in the transport and packing container. Conveniently, the transport and packaging container or a plurality of transport and packaging containers is placed in a packaging unit in step S26, for example, by sealing a packaging bag made of a sterile plastic material. Afterwards, this packaging unit may be closed in step S27, for example, by welding, and the outside of the packaging unit may be sterilized. Finally, this packaging unit is then removed from the clean room with the higher particle concentration in step S28 and delivered to a customer.

Between the step S12 (coupling the transport container . . . ) and S14 (opening the transfer port door . . . ) optionally an additional step may be carried out for sterilizing especially the front side wall of the transport container with the cover or protective sheet provided thereon. Suitable processes for this purpose are in particular: purging the front side wall with a flow of ethylene oxide gas (ETO), irradiating the front side wall using gamma radiation or an electron beam, purging the front side wall with vapor (under controlled conditions), or newer methods, such as oxidative low temperature sterilization. For this purpose, corresponding sterilization devices may be provided on the outside of the clean room with the lower concentration of particles in the region of the transfer port door, in particular gas outlets or irradiation devices. Preferably, the sterilization is carried out only after sealing the gap between the front side wall of the transport container and the side wall of the clean room against the environment. Generally, however, the sterilization may also be carried out without sealing this gap, in particular if the transport container has been placed in such a close proximity to the side wall, that the width of the gap is already relatively small in comparison with the dimensions of the transport container.

For a classification of the aforementioned clean rooms the ISO 14644-1 standard is hereby expressly referred to. Depending on the further processing of the containers and/or on the substances to be stored in this clean room a suitable cleanliness is selected as a cleanliness (clean room class) in this clean room with the lower particle concentration. The present invention contemplates especially clean room class 3 of ISO 14644-1, more preferably clean room class 2 of ISO 14644-1, and even more preferably clean room class 1 of ISO 14644-1. The transport and packaging container and the containers accommodated therein may be delivered under conditions of an appropriate clean room class and/or may be delivered again sterile packaged under the conditions of an appropriate clean room class.

Conveniently, the clean room class of the space or clean room upstream of the clean room with the lower particle concentration is worse, preferably one class of ISO 14644-1 worse than the clean room class of the clean room with the lower particle concentration. The classification of the aforementioned clean rooms may also be performed in a corresponding manner in accordance with GMP (Good Manufacturing Practice), where GMP class A represents the best clean room class and GMP class D represents the worst clean room class.

Of course, according to the present invention the controlled transfer of the containers into a clean room may also be carried out several times successively.

As will become apparent to the person skilled in the art upon reading the above description, generally also a gas-impermeable protective sheet may be used as a cover on the front end face of the transport container instead of the gas-permeable protective sheet, for example, a foil of aluminum or plastic or a metal-plastic composite material, which is bonded on one or two front end faces of the transport container. As an alternative, lids, flaps or openable flaps, doors or openable folding mechanisms may be used, which are made of a plastic or metal and properly close the access opening on the front end face of the transport container, which are, for example, plugged into this access opening or can be displaced into a closed position by means of a pivoting, folding or sliding movement.

As will become apparent to the person skilled in the art upon studying the above description, particularly the following advantages may be accomplished according to the present invention: the packaging can be packaged and unpacked like an onion, layer by layer; the packaging can be coupled to a port, for example, between two clean rooms or sterile rooms, can be sterilized at the inside using a gas flowing in via a gas-permeable protective sheet, and may be unpacked again; preferably the loading and unloading is performed via side walls, i.e. laterally, so that the containers are not tilted or rotated; according to the present invention the use of inverting plates is not necessary; box-shaped transport and packaging containers are mechanically stable and can be stacked one above the other; the transport and packaging containers are hermetically sealed and can be opened, unloaded and sealed again easily if a flap is provided on the front surface thereof; the transport and packaging containers can be manufactured easily and at low costs, due to a simple contour/geometry (which is e.g. box shaped); the transport and packaging containers particularly may be provided with a gas-permeable protective sheet as described above, so that these can be sterilized in a sealed condition, in particular by a flow of a sterilizing gas or vapor; protective sheets or covers, such as flaps, may be provided on both front faces of a transport and packaging container, so that it can be loaded and unloaded selectively from either front face, for example, by displacing and sliding a supporting structure as described above.

As will become apparent to the person skilled in the art when studying the above description, not only pharma containers and/or closure elements can be aseptically introduced into a clean room using the aforesaid method, but it is also possible to discharge packaging materials (i.e. waste) out of a clean room in a corresponding manner. The bags/tubs and, if necessary, also nests may also be transferred out of the insulator or clean room used for the further processing of the pharmaceutical containers easily.

Although it has been described above that the transfer port door of the clean room is pivotally mounted, the access opening to the clean room may be closed and sealed in a corresponding manner by means of other closure elements known from the prior art; for example, such closure elements may be displaced hydraulically in vertical or horizontal direction for providing access to the access opening of the clean room, similar to a plate valve for vacuum systems.

As will become readily apparent to the person skilled in the art upon reading the foregoing description, according to the present invention the features and aspects described above can be combined with each other also in a manner different than specifically disclosed in the foregoing. Such further embodiments shall be construed to be covered by the scope of protection of the appended claims as well, provided that these make use of the general approach of the present invention, as claimed in the appended claims.

LIST OF REFERENCE NUMBERS

| | |
|---|---|
| 1 | transport container |
| 2 | upper side |
| 3 | bottom side |
| 4 | longitudinal side |
| 5 | side wall |
| 5a | front side wall |
| 5b | rear side wall |
| 6 | edge |
| 7 | elastic seal |
| 8 | adhesive rim |
| 9 | access opening |
| 10 | cover/protective sheet |
| 11 | flange |
| 12 | protrusion |
| 120 | step |
| 13 | recess |
| 130 | additional recess |
| 14 | opening with gas-permeable protective sheet |
| 15 | front side wall |
| 16 | beveled edge |
| 17 | lid |
| 18 | beveled edge |
| 19 | resilient tab |
| 20 | guide rail |
| 24 | outer sealed space |
| 26 | recess |
| 27 | holding web |
| 29 | gap |
| 30 | side wall of second clean room B |
| 300 | opening of second clean room B |
| 301 | clamping rail |
| 302 | front limiting wall of clamping rail 301 |
| 303 | side wall of clamping rail 301 |
| 304 | clamping channel |
| 305 | stop or supporting surface |
| 308 | adjustable clamping device |
| 309 | adjustable clamping device |
| 31 | beveled edge |
| 32 | transfer port door |
| 33 | beveled edge |
| 34 | sealing element |
| 35 | swivel arm |
| 36 | pivot axis |
| 37 | circumferential projection |
| 38 | elastic sealing member |
| 39 | elastic sealing member |
| 40 | holding arm |
| 41 | heater |
| 42 | suction port |
| 43 | suction line |
| 44 | connecting line to suction device (not shown) |
| 45 | latching arm |
| 46 | pivot axis |
| 47 | latching element |
| 50 | guide rail |
| 55 | supporting structure |
| 58 | packaging bag |
| 59 | internal volume of packaging bag 58 |
| 60 | upper part |
| 61 | bottom of upper part 60 |
| 62 | side wall of upper part 60 |
| 63 | front/rear side wall of upper part 60 |
| 65 | side wall |
| 66 | transverse web |
| 67 | receptacle |
| 68 | bottom edge |
| 70 | bottom part |

-continued

LIST OF REFERENCE NUMBERS

| | |
|---|---|
| 71 | bottom of bottom part 70 |
| 72 | side wall of bottom part 70 |
| 73 | front/rear side wall of bottom part 70 |
| 74 | side wall |
| 75 | transverse web |
| 76 | front side flap |
| 77 | receptacle |
| 78 | protrusion |
| 80 | intermediate part |
| 81 | bottom of intermediate part 80 |
| 83 | front side wall of intermediate part 80 |
| 84 | side wall of intermediate part 80 |
| 85 | reinforcement of rim |
| 86 | predetermined breaking line/line-shaped weakened region |
| 87 | inner circumferential portion |
| 88 | outer circumferential portion |
| 90 | supporting structure |
| 91 | opening |
| 92 | holding arm |
| 93 | hinge |
| 94 | pivotable edge of supporting structure |
| 95a | projection |
| 95b | recess |
| 100 | container |
| 101 | bottom of container 100 |
| 102 | side wall of container 100 |
| 103 | constricted neck portion of container |
| 104 | widened upper rim of container 100 |
| 105 | filling opening of container 100 |
| A | first clean room |
| B | second clean room |
| C | third clean room |

What is claimed is:

1. A method for transferring a plurality of containers for storage of substances for medical, pharmaceutical or cosmetic purposes and/or closure elements of such containers from a transport and packaging container into a clean room, wherein the transport and packaging container has a side wall having an access opening, which is sterile sealed by a gas-permeable protective sheet or gas-permeable cover, the method comprising the steps of:

placing the transport and packaging container together with the plurality of containers and/or closure elements accommodated therein, so that the side wall of the transport and packaging container is disposed directly at a side wall of the clean room and in close proximity to a transfer port door of the clean room;

opening the transfer port door, wherein by coupling the gas-permeable protective sheet or gas-permeable cover with the transfer port door the gas-permeable protective sheet or gas-permeable cover is separated from the side wall of the transport and packaging container at the same time so that the access opening of the transport and packaging container is in communication with an inside space of the clean room;

transferring the plurality of containers and/or the closure elements from the transport and packaging container into the inside space of the clean room; and closing the transfer port door.

2. The method as claimed in claim 1, wherein the side wall of the transport and packaging container is placed so close to the side wall of the clean room that a gap between the side wall of the transport and packaging container and the side wall of the clean room is sealed by a sealing element.

3. The method as claimed in claim 2, wherein the sealing element is an elastic sealing element, which is disposed on the side wall of the transport and packaging container and/or on the side wall of the clean room.

4. The method as claimed in claim 1, wherein the coupling of the gas-permeable protective sheet or gas-permeable cover with the transfer port door is performed by latching, by temporarily fixing the gas-permeable protective sheet or gas-permeable cover on an outside of the transfer port door by adjustable grippers or by sucking the gas-permeable protective sheet or gas-permeable cover against the outside of the transfer port door by suction devices.

5. The method as claimed in claim 1, wherein the gas-permeable protective sheet is a gas-permeable plastic film consisting of a mesh of plastics fibers that is bonded to the side wall of the transport and packaging container.

6. The method as claimed in claim 1, wherein the cover, when present, has a gas-impermeable frame having an opening, which is sterile sealed by a gas-permeable plastic film, or wherein the gas-permeable protective sheet, when present, is a gas-permeable plastic film consisting of a mesh of plastics fibers that is bonded to the side wall of the transport and packaging container.

7. The method as claimed in claim 5, comprising the further step of sterilizing an inside space of the transport and packaging container and/or the containers accommodated therein and/or the closure elements by a flow of a gas or vapor through the gas-permeable protective sheet.

8. The method as claimed in claim 6, comprising the further step of sterilizing an inside space of the transport and packaging container and/or the containers accommodated therein and/or the closure elements by a flow of a gas or vapor through the gas-permeable protective sheet.

9. The method as claimed in claim 5, wherein a heating device is disposed at the transfer port door in correspondence with an adhesive rim along which the gas-permeable plastic film is bonded to an edge of the side wall of the transport and packaging container, wherein:
the adhesive rim is heated and softened by activating the heating device, and
the gas-permeable plastic film is coupled with the transfer port door in such a manner that the gas-permeable plastic film is pulled off from the side wall of the transport and packaging container by opening the transfer port door after the softening of the adhesive rim.

10. The method as claimed in claim 6, wherein a heating device is disposed at the transfer port door in correspondence with an adhesive rim along which the gas-permeable plastic film is bonded to the frame, wherein
the adhesive rim is heated and softened by activating the heating device, and
the gas-permeable plastic film is coupled with the transfer port door in such a manner that the gas-permeable plastic film is pulled off from the frame by opening the transfer port door after the softening of the adhesive rim.

11. The method as claimed in claim 5, wherein:
the gas-permeable protective sheet is disposed on the side wall of the transport and packaging container,
a plurality of recesses or depressions is formed in the side wall of the transport and packaging container,
adjustable gripping devices corresponding to the recesses or depressions are disposed on an outside of the transfer port door,
the gripping devices are adjusted such that, in a first position of the gripping devices, the transport and packaging container is brought freely to a vicinity of the transfer port door of the clean room,
the gripping devices are then adjusted to a second position, in which the gripping devices engage with the corresponding recesses or depressions in the side wall of the transport and packaging container behind the gas-permeable protective sheet for temporarily fixing the gas-permeable protective sheet to the transfer port door,
the transfer port door is opened in the second position of the gripping devices, and
the gripping devices are adjusted back to the first position after closing the transfer port door.

12. The method as claimed in claim 6, wherein:
the gas-permeable protective sheet is disposed on a frame-like projection formed on the side wall of the transport and packaging container,
a plurality of recesses or depressions is formed in the frame-like projection,
adjustable gripping devices corresponding to the recesses or depressions are disposed on an outside of the transfer port door,
the gripping devices are adjusted such that, in a first position of the gripping devices, the transport and packaging container is brought freely to a vicinity of the transfer port door of the clean room,
the gripping devices are then adjusted to a second position, in which the gripping devices engage with the corresponding recesses or depressions in the frame-like projection behind the gas-permeable protective sheet for temporarily fixing the gas-permeable protective sheet to the transfer port door,
the transfer port door is opened in the second position of the gripping devices, and
the gripping devices are adjusted back to the first position after closing the transfer port door.

13. The method as claimed in claim 1, wherein all the containers and/or the closure elements are supported in a supporting structure which is accommodated in said transport and packaging container and wherein the supporting structure together with the containers and/or the closure elements supported by it are transferred from the transport and packaging container into the inside space of the clean room by shifting.

14. The method as claimed in claim 13, wherein the supporting structure comprises a box-shaped bottom part having a bottom, on which the containers are directly supported, and wherein the box-shaped bottom part is shifted directly on a bottom of the transport and packaging container and transferred to the clean room.

15. The method as claimed in claim 13, wherein the supporting structure comprises a box-shaped upper part, which rests directly, or indirectly with interposition of an intermediate part, on upper ends of the containers.

16. The method as claimed in claim 1, wherein the transport and packaging container is provided sterile packaged inside a sterile packaging bag and wherein a first space is disposed upstream of the clean room, said first space having a higher concentration of particles, said method further comprising the steps of:
sterilizing an outside of the packaging bag in the first space; and
removing the transport and packaging container from the sterile packaging bag after the step of sterilizing.

17. The method as claimed in claim 16, wherein the plurality of containers is transferred back into the transport and packaging container after a further processing in the clean room by the following steps:

placing the transport and packaging container in the first space having the higher concentration of particles, so that the side wall of the transport and packaging container with the access opening is arranged directly at the side wall of the clean room and in close proximity to the transfer port door of the clean room;

opening the side wall of the transport and packaging container and the transfer port door so that the access opening of the transport and packaging container communicates with the inside space of the clean room;

transferring the plurality of containers from the inside space of the clean room into the transport and packaging container;

closing the transfer port door; and closing the transport and packaging container by the cover.

18. The method as claimed in claim 16, wherein the first space is a first clean room having a higher concentration of particles than the clean room.

19. The method as claimed in claim 17, wherein closing the transport and packaging container by the cover is caused by a simultaneous closing of the transfer port door.

20. The method as claimed in claim 17, further comprising:

sterilizing an outside of the transport and packaging container in the first space having the higher concentration of particles after transferring the plurality of containers into the transport and packaging container;

inserting the transport and packaging container into the sterile packaging bag after the step of sterilizing the outside; and sealing the sterile packaging bag.

21. The method as claimed in claim 20, wherein the first space is a first clean room having a higher concentration of particles than the clean room.

* * * * *